United States Patent [19]

Yamamoto et al.

[11] 4,318,850

[45] Mar. 9, 1982

[54] CARBOXAMIDE TYPE AZOMETHINE PIGMENTS

[75] Inventors: Fumihiko Yamamoto, Kawasaki; Mitsuru Katayose; Kyugo Tanaka, both of Yokohama; Teruyuki Misumi, Kawasaki, all of Japan

[73] Assignee: Asahi Kasei Kogyo Kabushiki Kaisha, Osaka, Japan

[21] Appl. No.: 148,498

[22] Filed: May 9, 1980

[30] Foreign Application Priority Data

May 16, 1979 [JP] Japan .................. 54-59110

[51] Int. Cl.³ .............. C09B 43/155; C09B 55/00; C09B 57/04; D06P 1/13
[52] U.S. Cl. ............................. 260/152; 260/157; 260/205; 260/206; 260/208; 546/159; 548/325
[58] Field of Search ......... 260/152, 157, 165, 325 PH, 260/326 A, 326 D, 326 HL, 326 S, 326 N, 326.1

[56] References Cited

U.S. PATENT DOCUMENTS

| | | | |
|---|---|---|---|
| 2,537,352 | 1/1951 | Jones ........................ | 260/326 N |
| 2,725,385 | 11/1955 | Seeger et al. ............... | 260/326 N |
| 2,973,358 | 2/1961 | Pugin ....................... | 260/325 PH X |
| 3,787,438 | 1/1974 | Thomas ..................... | 260/325 PH |
| 3,867,404 | 2/1975 | Von Der Crone et al. ... | 260/325 PH |
| 3,971,805 | 7/1976 | Model ....................... | 260/325 PH |
| 4,006,162 | 2/1977 | Model ....................... | 260/325 PH |
| 4,008,097 | 2/1977 | Bitterli et al. ............. | 260/325 PH X |
| 4,223,152 | 9/1980 | Fujii et al. ................. | 260/325 PH X |

FOREIGN PATENT DOCUMENTS

| | | |
|---|---|---|
| 2525587 | 12/1975 | Fed. Rep. of Germany ...... 260/325 PH |
| 2606311 | 1/1976 | Fed. Rep. of Germany ... 260/326.1 |
| 2903709 | 8/1979 | Fed. Rep. of Germany ...... 260/325 PH |

*Primary Examiner*—Floyd D. Higel
*Attorney, Agent, or Firm*—Finnegan, Henderson, Farabow, Garrett & Dunner

[57] ABSTRACT

A compound of the formula,

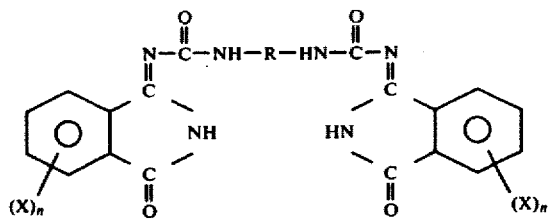

wherein R is an aromatic compound selected from the group consisting of:

-continued

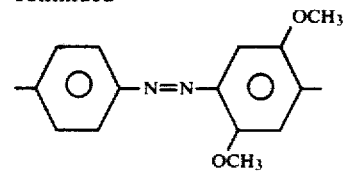

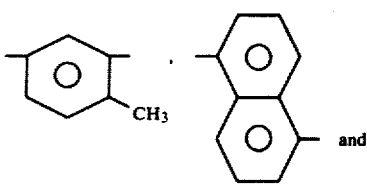

and wherein $R_1$, $R_2$, $R_3$, $R_4$, $R_5$, $R_6$ and $R_7$ which may be the same or different, are each selected from the group consisting of hydrogen, chlorine, a $C_{1-2}$ alkyl group and a $C_{1-2}$ alkoxy group and wherein Y is $-SO_2-$, $-O-$, $-S-$, $-CO-$, $-N=N-$ or $-NHCO-$; X is a halogen atom selected from the group consisting of chlorine, bromine, and fluorine; and n is zero or an integer of from 1 to 4. The compound is useful for pigments having hue from the yellow shade to the red shade and having especially high chroma. The pigments also have improved weather resistance, chemical resistance and tinting strength.

43 Claims, 22 Drawing Figures

CARBOXAMIDE TYPE AZOMETHINE PIGMENTS

BACKGROUND OF THE INVENTION

1. Field of the Invention

The present invention relates to a new organic compound and to a process for their production. More particularly, it relates to a new carboxamide type azomethine organic compound which is useful as a pigment.

2. Description of the Prior Art

An isoindolinone type pigment which is obtained by reacting 3-iminoisoindoline-1-one with aromatic diamine compound is shown in Japanese Patent Publications No. 4488/1959 and 3826/1961 and Japanese Patent Application (OPI) No. 11922/1978. A bispyrropyrazine pigment which is obtained by reacting aromatic diisocyanate with pyrropyrazine compound is also shown in Japanese Patent Application (OPI) No. 83026/1979. But a carboxamide type azomethine pigment which is obtained by reacting 3-imino-isoindoline-1-one compound with aromatic diisocyanate compound has not been known previously.

SUMMARY OF THE INVENTION

The present invention in one embodiment provides a new organic compound represented as general formula [I]:

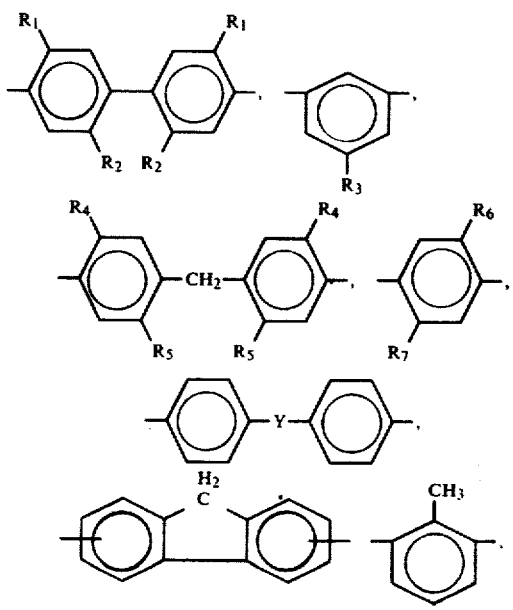

wherein R is a residue of a substituted or unsubstituted aromatic compound selected from the group consisting of:

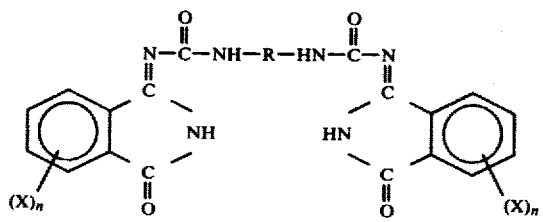

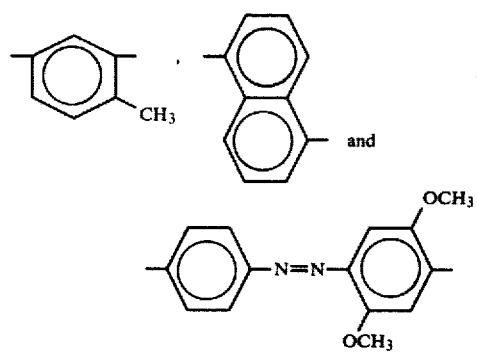

wherein $R_1$, $R_2$, $R_3$, $R_4$, $R_5$, $R_6$ and $R_7$, which may be the same or different, are each selected from the group consisting of hydrogen, chlorine, a $C_{1-2}$ alkyl group, a $C_{1-2}$ alkoxy group and Y is $-SO_2-$, $-O-$, $-S-$, $-CO-$, $-N=N-$ or $-NHCO-$; X is a halogen atom selected from the group consisting of chlorine, bromine, and fluorine; and n is zero or an integer of from 1 to 4.

The present invention is another embodiment provides a method of producing the new organic compound as described above which comprises reacting about 2 moles of 3-iminoisoindoline-1-one compound represented by the general formula [II]:

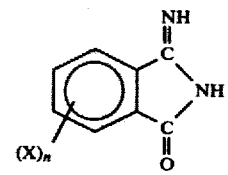

wherein X is a halogen atom selected from the group consisting of chlorine, bromine and fluorine; n is zero or an integer of from 1 to 4, with about 1 mole of diisocyanate compound represented by the general formula [III]:

O=C=N—R—N=C=O wherein R is a residue of a substituted or unsubstituted aromatic compound selected from the group consisting of:

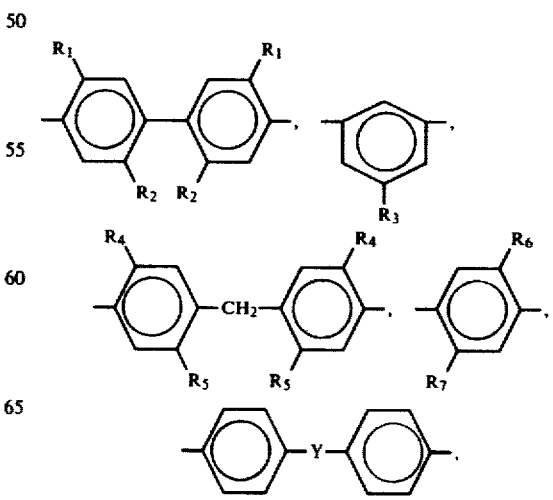

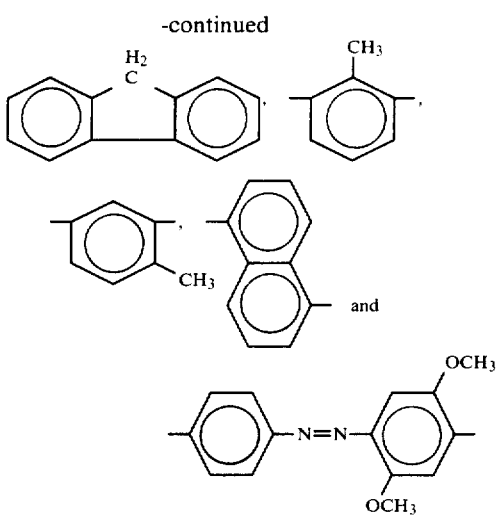

wherein $R_1$, $R_2$, $R_3$, $R_4$, $R_5$, $R_6$ and $R_7$, which may be the same or different, each is hydrogen, chlorine, a $C_{1-2}$ alkyl group, a $C_{1-2}$ alkoxy group and Y is $—SO_2—$, $—O—$, $—S—$, $—CO—$, $—N=N—$ or $—NHCO—$.

DESCRIPTION OF PREFERRED EMBODIMENT

Figure 1:
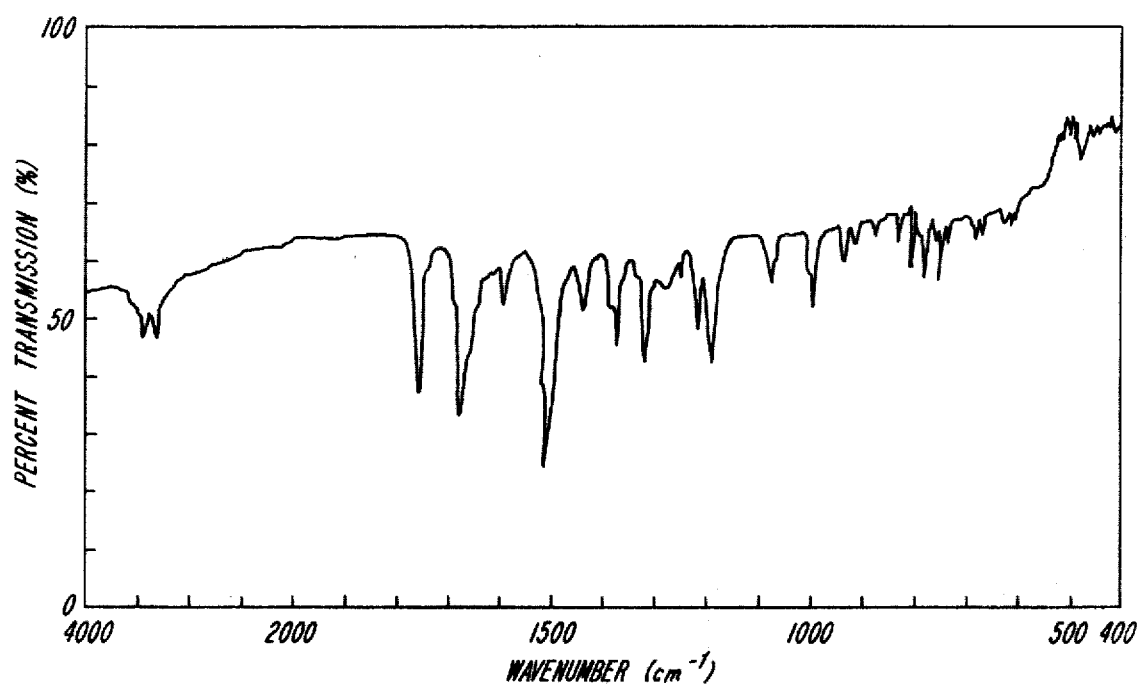
FIGS. 1-22 illustrate infrared absorption spectra of compounds obtained by the examples of this invention.

New structure—compounds represented by general formula [I] are useful pigments having various kinds of color according to the kinds of groups in the formula. For example, a compound having the formula:

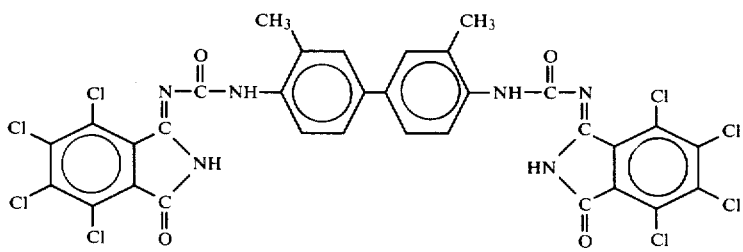

is a superior red-pigment having excellent properties such as weather proofing, heat resistance, solvent resistance and migration resistance. A somewhat similar compound having the formula:

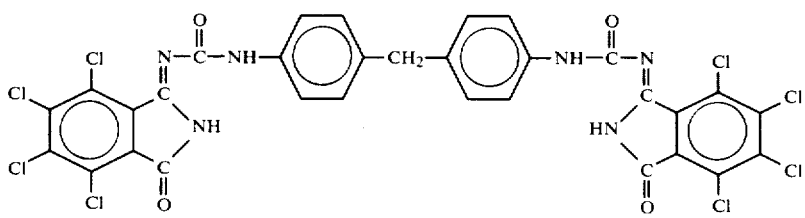

is a rich yellow pigment having excellent properties.

New compounds represented by general formula [I] have hue from the yellow shade to the red shade and have especially high chroma. The other properties of the pigment such as weather resistance, chemical resistance and tinting strength are greater than those of modern pigment being commercially available.

Suitable examples of 3-iminoisoindoline-1-one compound represented by general formula [I] of this invention include 3-imino-4,5,6,7-tetrachloroisoindoline-1-one, 3-iminoisoindoline-1-one, 3-imino-4,7-dichloroisoindoline-1-one, 3-imino-4,5,7-trichloroisoindoline-1-one, 3-imino-4,6,7-trichloroisoindoline-1-one, 3-imino-4,5,6,7-tetrabromoisoindoline-1-one and 3-imino-4,5,6,7-tetrafloroisoindoline-1-one. In these examples, 3-imino-4,5,6,7-tetrachloroisoindoline-1-one is prefered because it is a remarkably excellent pigment. 3-imino-4,5,6,7-tetrachloroisoindoline-1-one is produced by hydrolyzing tetrachlorophthalonitrile in a mixed medium of acetone and water in the presence of ammonia and hydrogen peroxide as catalyst. The tetrachlorophthalonitrile is produced by gas phase chlorination of phthalonitrile in the presence of active carbon as catalyst as described, for example, in Japanese Patent Publication No. 23330/1961.

Suitable examples of diisocyanate compounds represented by general formula [III] include 3,3'-dimethyl-4,4'-diphenyldiisocyanate, 3,3'-dimethoxy-4,4'-diphenyldiisocyanate, 3,3'-dichloro-4,4'-diphenyldiisocyanate, 2,2'-dichloro-5,5'-dimethyl-4,4'-diphenyldiisocyanate, 2,2',5,5'-tetrachloro-4,4'-diphenyldiisocyanate, 4,4'-diphenylether diisocyanate, 4,4'-diphenylsulfone diisocyanate, 4,4'-diphenylsulfide diisocyanate, 4,4'-benzophenone diisocyanate, 4,4'-azobenzene diisocyanate, 4,4'-benzanilide diisocyanate, p-phenylene diisocyanate, 2-methyl-p-phenylene diisocyanate, 2-chloro-p-phenylene diisocyanate, 2-methoxy-p-phenylene diisocyanate, 2,5-dimethyl-p-phenylene diisocyanate, 2,5-dichloro-p-phenylene diisocyanate, 2,5-dimethoxy-p-phenylene diisocyanate, m-phenylene diisocyanate, 3-methylbenzene-1,5-diisocyanate, 3-chlorobenzene-1,5-diisocyanate, 3-methoxybenzene-1,5-diisocyanate, 4,4'-diphenylmethane diisocyanate, 3,3'-dichloro-4,4'-diphenylmethane diisocyanate, 3,3'-dimethyl-4,4'-diphenylmethane diisocyanate, 3,3'-dimethoxy-4,4'-diphenylmethane diisocyanate, 2,2',5,5'-tetrachloro-4,4'-diphenylmethane diisocyanate, 2,2'-dichloro-4,4'-diphenylmethane diisocyanate, 1,5-naphthalene diisocyanate, 1,4-naphthalene diisocyanate, 2,6-toluene diisocyanate, 2,4-toluene diisocyanate, 2,7-fluorene diisocyanate, 3,6-fluorene diisocyanate, 1,5-anthraquinone diisocyanate, 1,4-anthraquinone diisocyanate, 2,6-pyridine diisocyanate, 2,5-pyridine diisocyanate, 2,7-carbazole diisocyanate, 2,8-benzofuran diisocyanate, 2,7-dibenzothiophene diisocyanate, 3,7-dibenzothiophene diisocyanate, dibenzothiophene-3,7-diisocyanate-5,5-dioxide, 4,4'-diphenylamine diisocyanate, 2-nitro-p-phenylene diisocyanate, 3,3'-diethyl-4,4'-diphenylmethane diisocyanate, 2-chloro-5-methoxybenzene-1,4-diisocyanate, 2,5-diethoxybenzene-1,4-diisocyanate, 3,3'-diethoxy-4,4'-diphenyl diisocyanate, 3-methyl-4,4'-azobenzene diisocyanate, 2-methoxy-4,4'-azobenzene diisocyanate, 2,5-dimethyl-4,4'-azobenzene diisocyanate, 2,5,2'-trimethyl-4,4'-azobenzene diisocyanate, 3-methyl-2'-methoxy-4,4'-azobenzene diisocyanate, 4-chloro-3,4'-azobenzene diisocyanate, 2-chloro-4,3'-azobenzene diisocyanate, 2-methyl-4,3'-azobenzene diisocyanate, 2-methoxy-4,3'-azobenzene diisocyanate, 2,4-azobenzene diisocyanate, 5-methoxy-2,4-azobenzene diisocyanate, 2,2'-dibenzyl diisocyanate, 3,8-pyrene diisocyanate, 2,8-chrysene diisocyanate, 2,9-naphthacene diisocyanate, 3,10-perylene diisocyanate, 4,7-benzoimidazole diisocyanate, 5,8-quinoline diisocyanate, 2,2'-bis(4-isocyanato phenyl)propane, triphenylene-4,4'-diisocyanate, p-terphenyl-4,4'-diisocyanate and so on.

The diisocyanate compounds mentioned above can be obtained by known methods such as by reacting diamino compounds with phosgene.

The reaction for producing the compound represented by the general formula [I] is carried out in an inert medium. Suitable examples of inert mediums which can be employed include chlorobenzene, O-dichlorobenzene, nitrobenzene, benzene, toluene, dioxane, acetonitrile, dibutylether, methylethylketone, anisole and so on. The inert medium mentioned above can be employed in any amount in which the reaction can be carried out conveniently. Preferably the medium is employed in amount of about 5 to about 30 times weight of 3-iminoisoindoline-1-one compound represented by the general formula [II] which is used as a starting material.

The reaction will be proceeded in the inert medium without a catalyst, but when a catalyst is added, the reaction is promoted. Suitable examples of catalysts which can be employed include a tertiary amine compounds such as N,N,N',N'-tetramethyl-1,6-hexanediamine, N,N,N',N'-tetramethyl-1,3-propanediamine, N,N,N'N'-tetramethyl-1,4-butanediamine, triethylamine, triethylenediamine, 1,8-diazabicyclo(5,4,0)undecene-7 and 1,6-diazabicyclo(4,3,0)monene-5 and organic tin compounds such as dibutyltin dilaurate, dimethyltin dichloride, trimethyltin hydroxide and n-buthyltin trichloride. The amount of the catalyst may be controlled in accordance with varieties of the catalyst and the diisocyanate. Usually amounts ranging from about 0.01 mole to about 1.0 mole based on one mole of diisocyanate compound are suitable.

The reaction temperature for production of the compound represented by the general formula [I] may be determined in accordance with activities of each chemicals. Temperature ranges from bout 0° C. to about 250° C., and preferably from about 50° C. to about 150° C. may be employed.

The reaction is normally carried out at atmosphere pressure, but reduced pressure may be used.

Preferably reaction is conducted by adding about 2 moles of 3-iminoisoindoline-1-one compound represented by the general formula [II] to about 1 mole of diisocyanate compound represented by the general formula [III]. However, the reaction also can be carried out by adding more than about 2 moles of the 3-iminoisoindoline-1-one compound, but in this case an excess amount of 3-iminoisoindoline-1-one compound must be removed after the reaction.

The compound represented by the general formula [I], obtained by the method mentioned above, itself can be used as pigment. According to usages, properties of the pigment, such as tinting strength, can be increased substantially by an additional grinding or pulverizing step.

The pigments comprising the compound of this invention have a clear hue of from the yellow shade to the red shade and a especially high chroma. The other properties of the pigment of this invention such as weather proofing, solvent resistance, chemical resistance and tinting strength are more than those of commercially available modern pigment having a hue of from the yellow shade to the red shade. Therefore, the pigment of this invention can be used as a coloring agent for paint, lacquer, plastics, printing ink and so on.

The compounds of this invention can be identified by an infrared absorption spectrum at around 1510 cm$^{-1}$ and 1670 cm$^{-1}$ caused by an urea bond, structure analysis by an nuclear magnetic resonance spectrum and a elementary analysis.

Hereinafter the present invention will be explained by examples, which are for purpose of illustration and are in no way limiting.

EXAMPLE 1

10.0 g of 3-imino-4,5,6,7-tetrachloroisoindoline-1-one, 4.65 g of 3,3'-dimethyl-4,4'-diphenyldiisocyanate and 200 g of O-dichlorobenzene as an inert solvent were taken up in a flask. The mixture was reacted under an atmosphere of nitrogen at 175° C. for 6 hours. A solid was filtered off, washed with N,N-dimethylformamide, acetone and water and dried at 120° C. As a result, 13.3 g of red pigment were obtained (a yield of 91%). Structure analyses of an infrared absorption spectrum and a nuclear magnetic resonance spectrum and an elementary analysis showed a structural formula as follows,

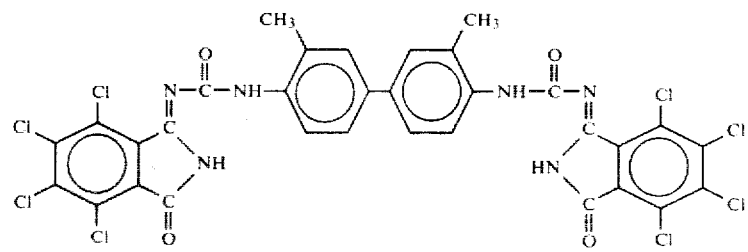

Conditions of structure analysis by nuclear magnetic resonance spectrum were as follows:
Device; PS-100 type manufactured by NIPPON DENSHI KABUSHIKI KAISHA
Width; 1080 Hz
Spectrograph; Proton 100 MHz
Solvent; Heavy hydrogenated dimethylformamide (7 heavy hydrogens)
Basic material; Tetramethylsilane
Temperature; 50° C.

Results of the elementary analysis were as follows,

|  | C | H | N | O | Cl |
|---|---|---|---|---|---|
| Calculated value (%) | 46.2 | 1.9 | 10.1 | 7.7 | 34.1 |
| Surveyed value (%) | 46.1 | 1.7 | 10.3 | 7.8 | 34.1 |

The absorption spectrum was shown in FIG. 1.

The pigment had a clear red color and had excellent properties such as a solvent resistance, a chemical resistance, a weather proofing and tinting strength.

This pigment was capable of use as a coloring agent for paint and a printing ink by known methods. Furthermore, articles colored by this pigment had excellent properties such as a weather proofing, a heat resistance and a migration resistance.

EXAMPLES 2 to 32

3-iminoisoindoline-1-one compounds, diisocyanate compounds and solvents were taken up and reacted according to the condition given in Table 1. The resulting products were treated in the same manner of example 1. The products obtained had structures represented by a general formula [I]. All pigments obtained had clear tints and had excellent properties such as a solvent resistance, weather proofing, heat resistance and migration resistance. The pigments obtained were examined according to standard JIS-K5101. The results are shown in Table 2.

TABLE 1

Figure 2:
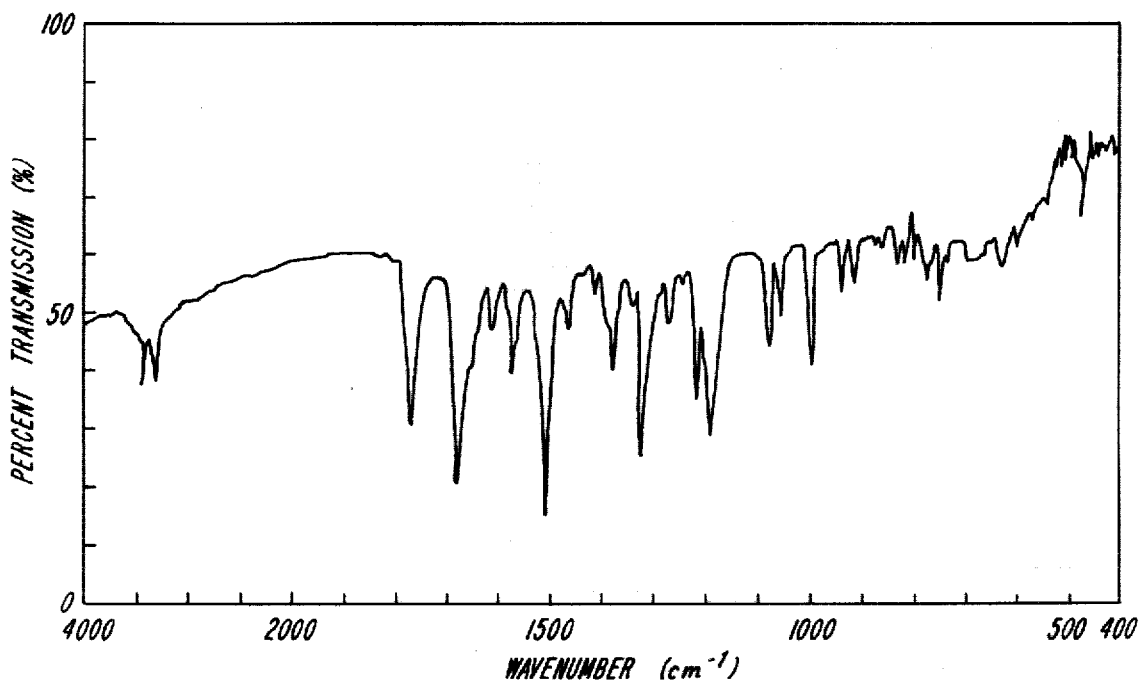
Figure 3:
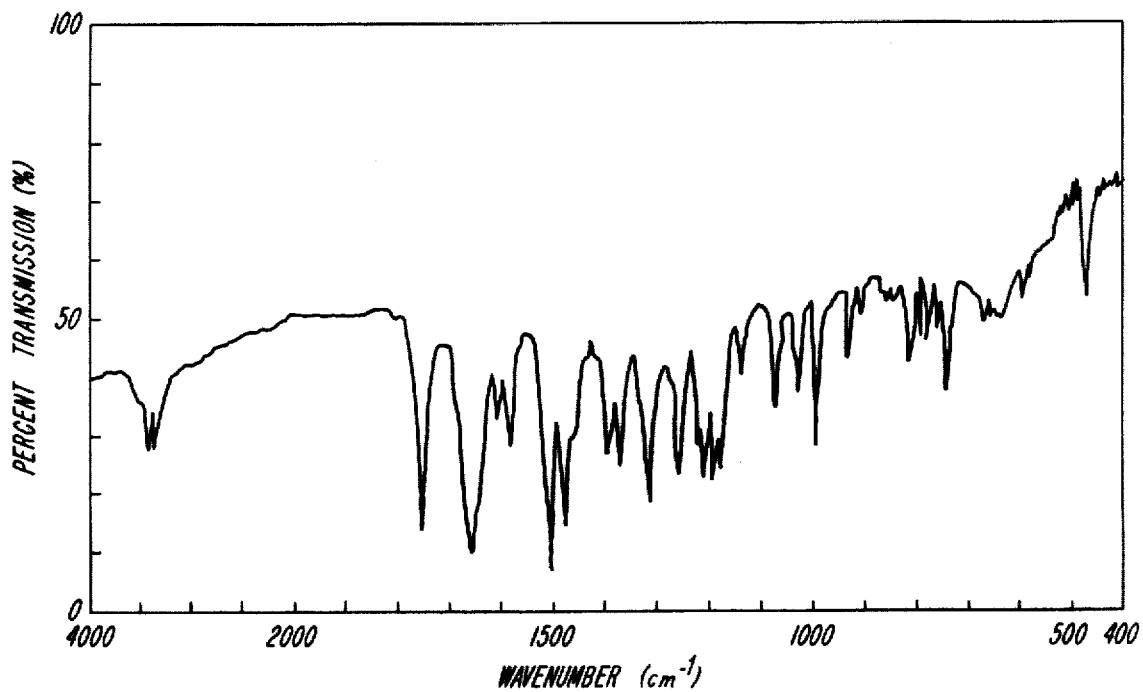
Figure 4:
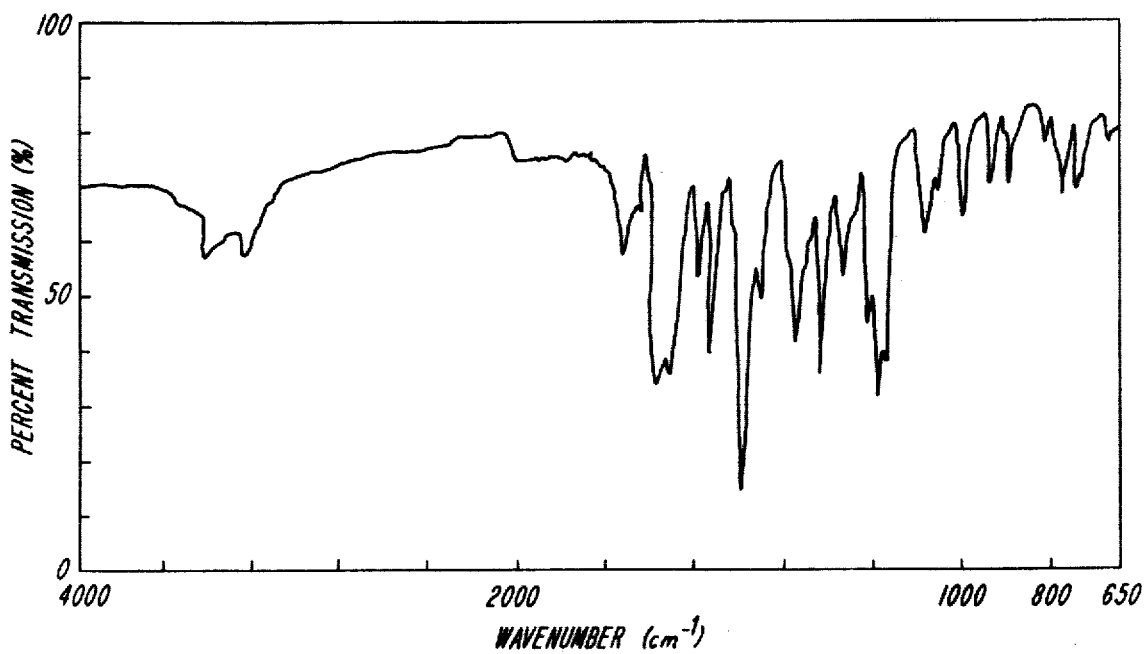
Figure 5:
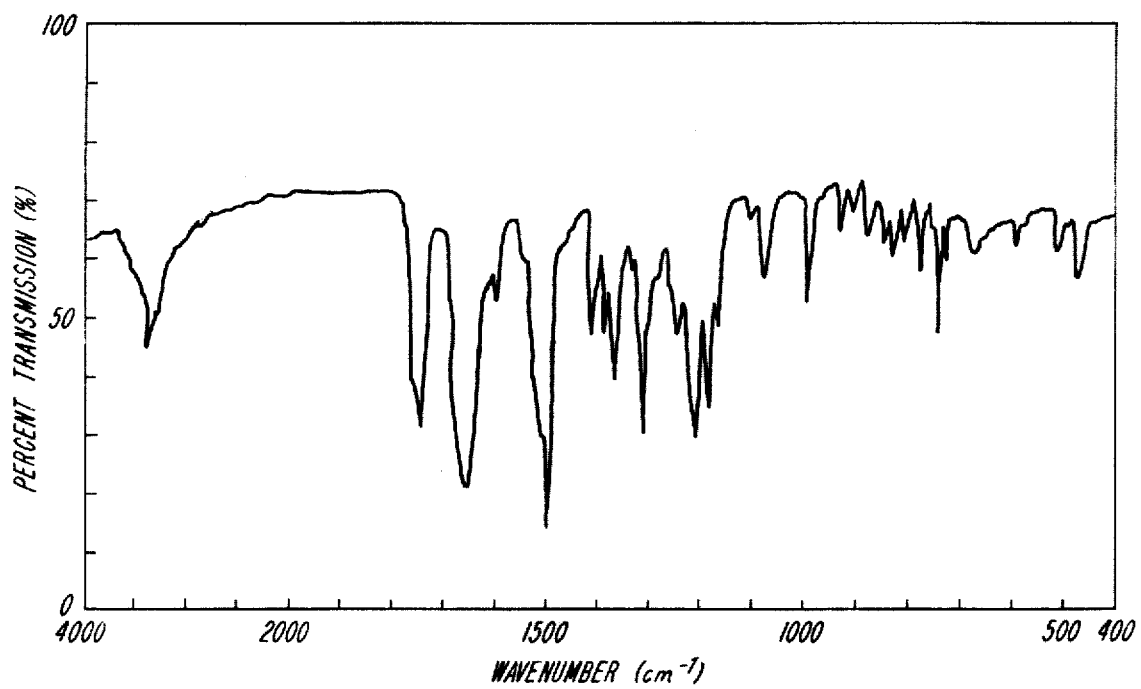
Figure 6:
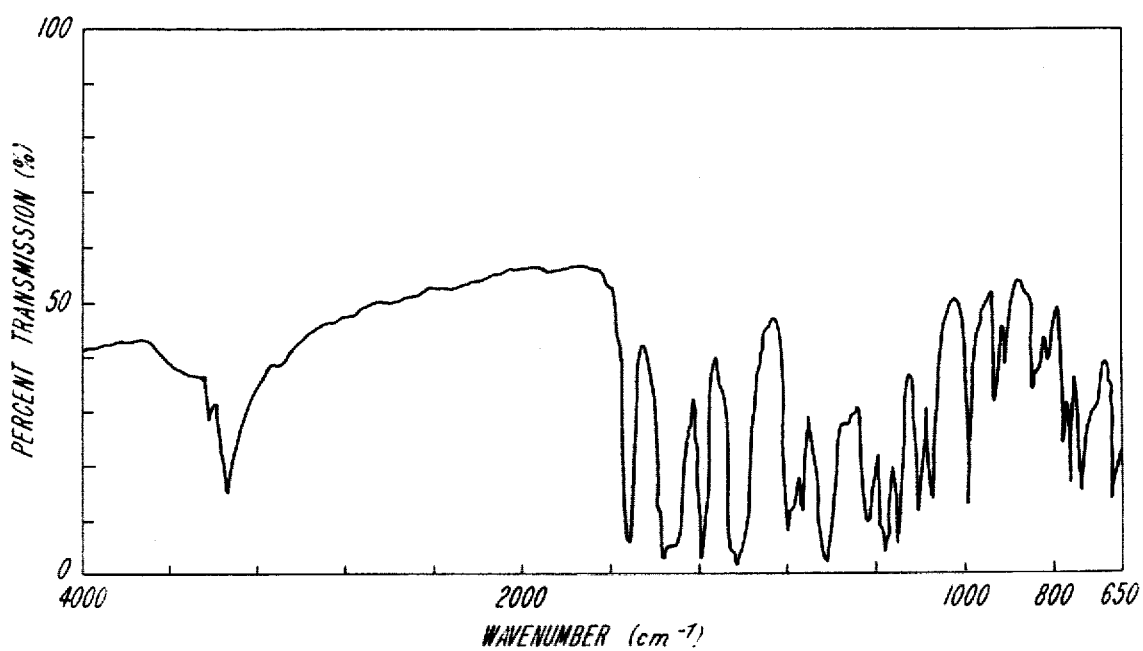
Figure 7:
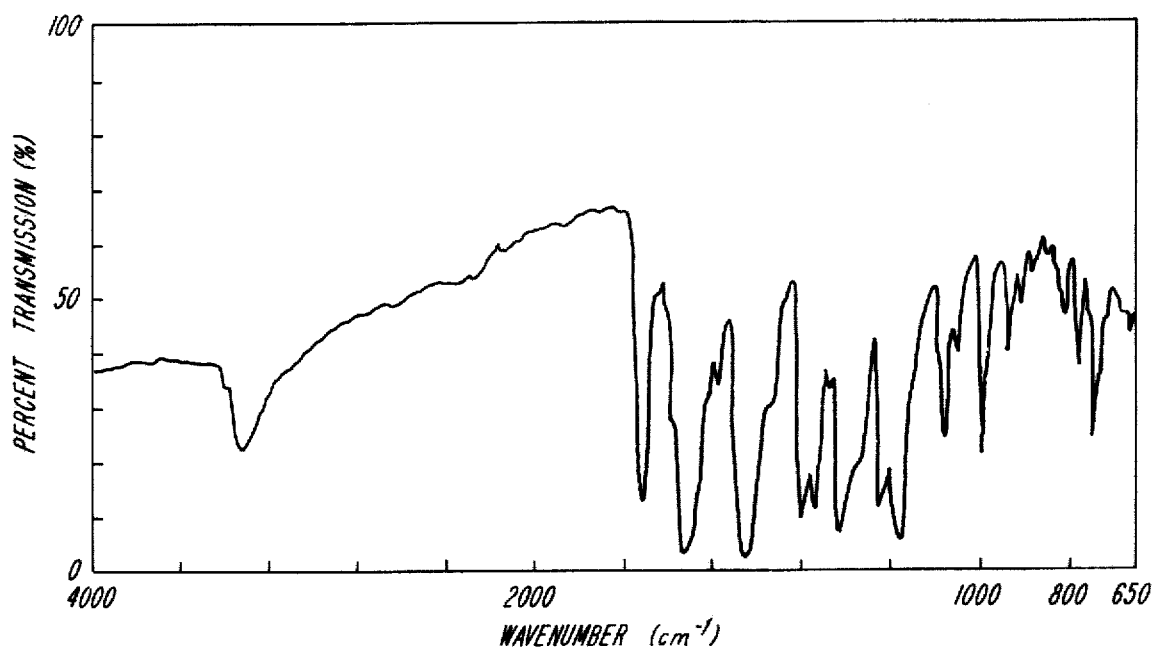
Figure 8:
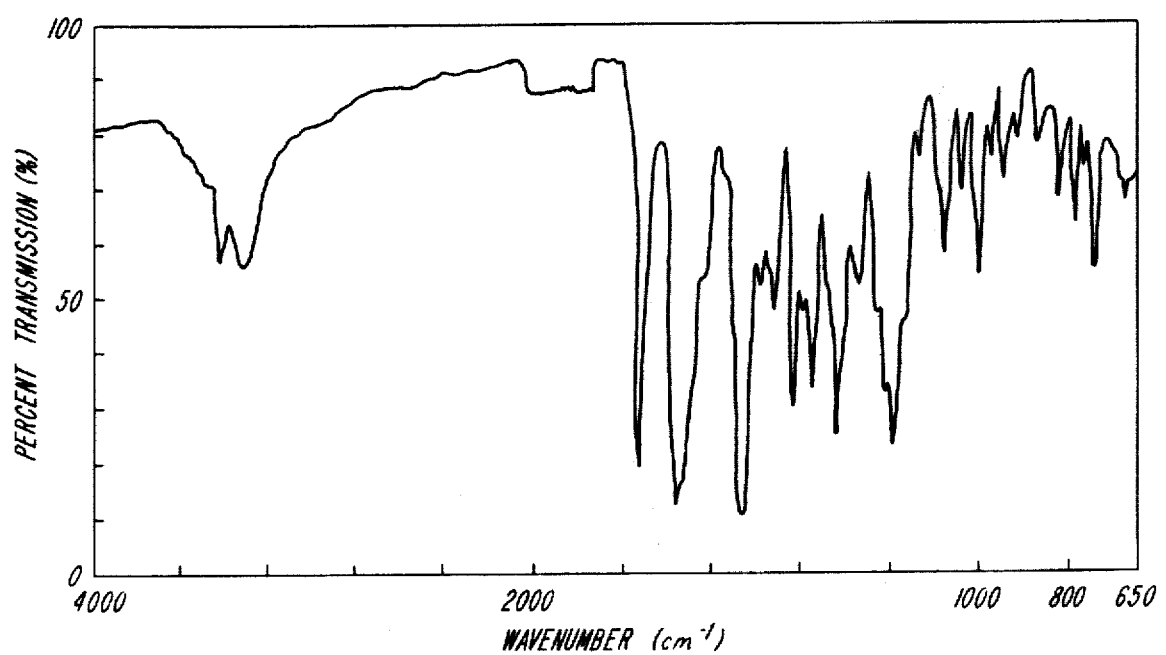

| Example No. | 3-Iminoisoindoline Compound Amount (g) | Diisocyanate Compound Amount (g) | Solvent Amount (g) | Reaction Temperature (°C.) | Condition Time (Hr) | Product Color | Yield (%) | Elementary Analysis Calculated (%) | Found (%) | Infrared Absorption Spectrum |
|---|---|---|---|---|---|---|---|---|---|---|
| 2 | 3-Imino-4,5,6,7-tetrachloro-isoindoline-1-one 10.0 | 3,3'-Dichloro-4,4'-diphenyl diisocyanate 5.37 | O-DCB(1) 200 | 175 | 6 | Red | 90 | C: 41.2 H: 1.1 N: 9.6 O: 7.3 Cl: 40.7 S: — | 41.9 1.0 9.4 7.5 40.2 — | FIG. 2 |
| 3 | 3-Imino-4,5,6,7-tetrachloro-isoindoline-1-one 10.0 | 3,3'-Dimethoxy-4,4'-diphenyl diisocyanate 5.21 | O-DCB 200 | 100 | 6 | Red | 87 | C: 44.4 H: 1.9 N: 9.7 O: 11.1 Cl: 32.9 S: — | 45.1 1.7 9.6 11.0 32.6 — | FIG. 3 |
| 4 | 3-Imino-4,5,6,7-tetrachloro-isoindoline-1-one 10.0 | 2,2',5,5'-Tetrachloro 4,4'-diphenyl diisocyanate 6.58 | O-DCB 200 | 175 | 6 | Yellow | 77 | C: 38.2 H: 0.8 N: 8.9 O: 6.8 Cl: 45.2 S: — | 38.3 0.9 9.1 6.7 45.0 — | FIG. 4 |
| 5 | 3-Imino-4,5,6,7-tetrachloro-isoindoline-1-one 14.2 | 4,4'-Diphenyl-ether diisocyanate 6.30 | O-DCB DBTL(2) 300 0.5 | 100 | 6 | Reddish Yellow | 93 | C: 43.9 H: 1.5 N: 10.2 O: 9.8 Cl: 34.6 S: — | 44.4 1.3 10.2 9.8 34.3 — | FIG. 5 |
| 6 | 3-Imino-4,5,6,7-tetrachloro-isoindoline-1-one 10.0 | 4,4'-Diphenyl-sulfone diisocyanate 5.28 | O-DCB 200 | 175 | 6 | Greenish Yellow | 60 | C: 41.5 H: 1.4 N: 9.7 O: 11.1 Cl: 32.7 S: 3.7 | 41.2 1.5 9.7 11.3 32.5 3.8 | FIG. 6 |
| 7 | 3-Imino-4,5,6,7-tetrachloro-isoindoline-1-one 10.0 | 4,4'-Diphenyl-sulfide diisocyanate 4.72 | O-DCB 200 | 175 | 6 | Red | 73 | C: 43.1 H: 1.4 N: 10.0 O: 7.7 Cl: 34.0 S: 3.8 | 42.2 1.6 10.2 7.9 34.2 3.9 | — |
| 8 | 3-Imino-4,5,6,7-tetrachloro-isoindoline-1-one 10.0 | 2-Chloro-p-phenylene diisocyanate 3.42 | O-DCB TMHD(3) 200 0.3 | 120 | 6 | Orange | 76 | C: 37.8 H: 0.9 N: 11.0 O: 8.4 Cl: 41.9 S: — | 37.5 0.9 11.0 8.5 42.1 — | FIG. 7 |
| 9 | 3-Imino-4,5,6,7-tetrachloro-isoindoline-1-one 10.0 | 2-Methyl-p-phenylene diisocyanate 3.06 | O-DCB TMHD(3) 200 0.3 | 120 | 6 | Orange | 76 | C: 40.4 H: 1.3 N: 11.3 O: 8.6 Cl: 38.3 S: — | 40.3 1.2 11.2 8.6 38.6 — | — |
| 10 | 3-Imino-4,5,6,7-tetrachloro-isoindoline-1-one | 2-Methoxy-p-phenylene diisocyanate 200 | O-DCB | 175 | 6 | Red | 81 | C: 39.6 H: 1.3 N: 11.1 | 39.3 1.2 11.1 | FIG. 8 |

TABLE 1-continued

Figure 9:
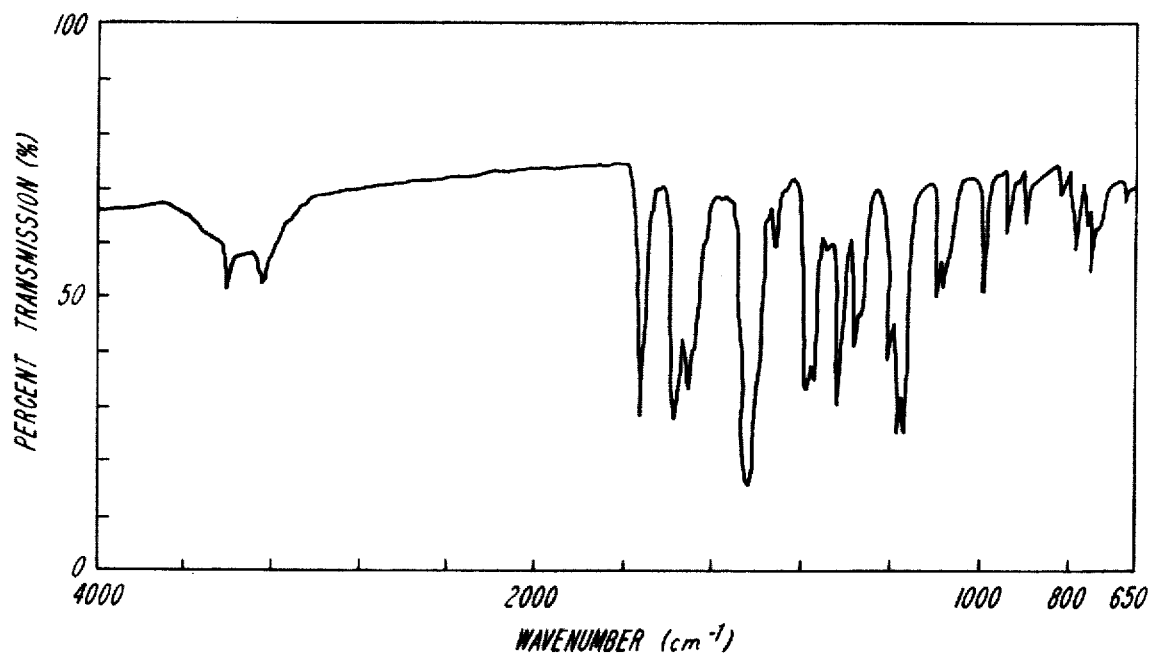
Figure 10:
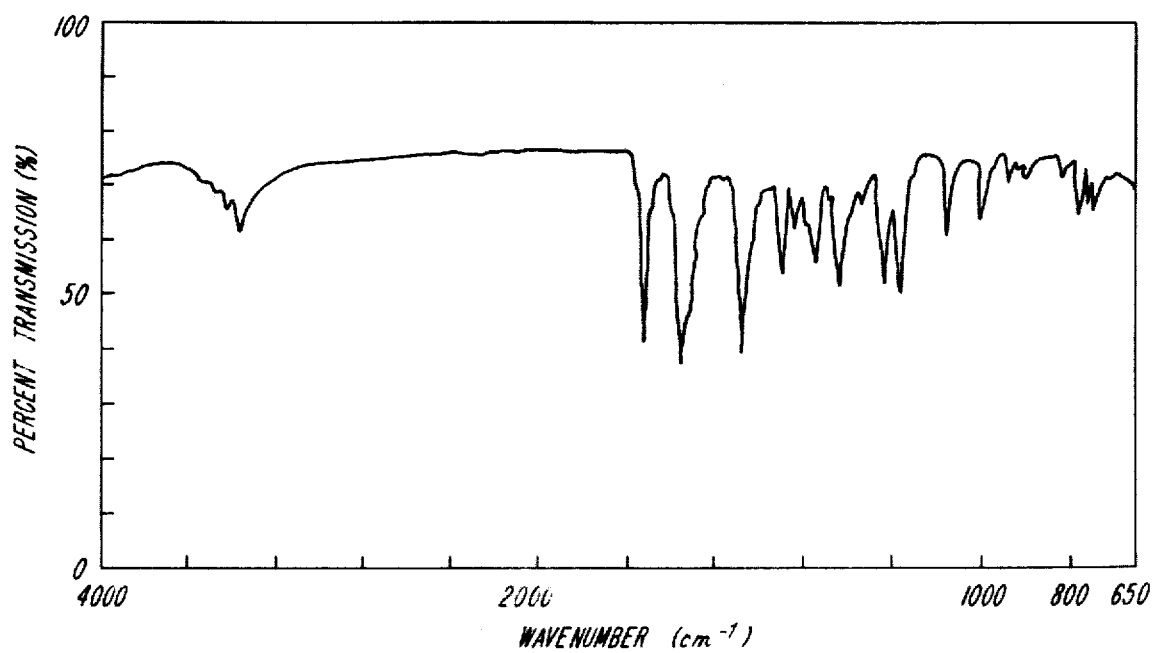
Figure 11:
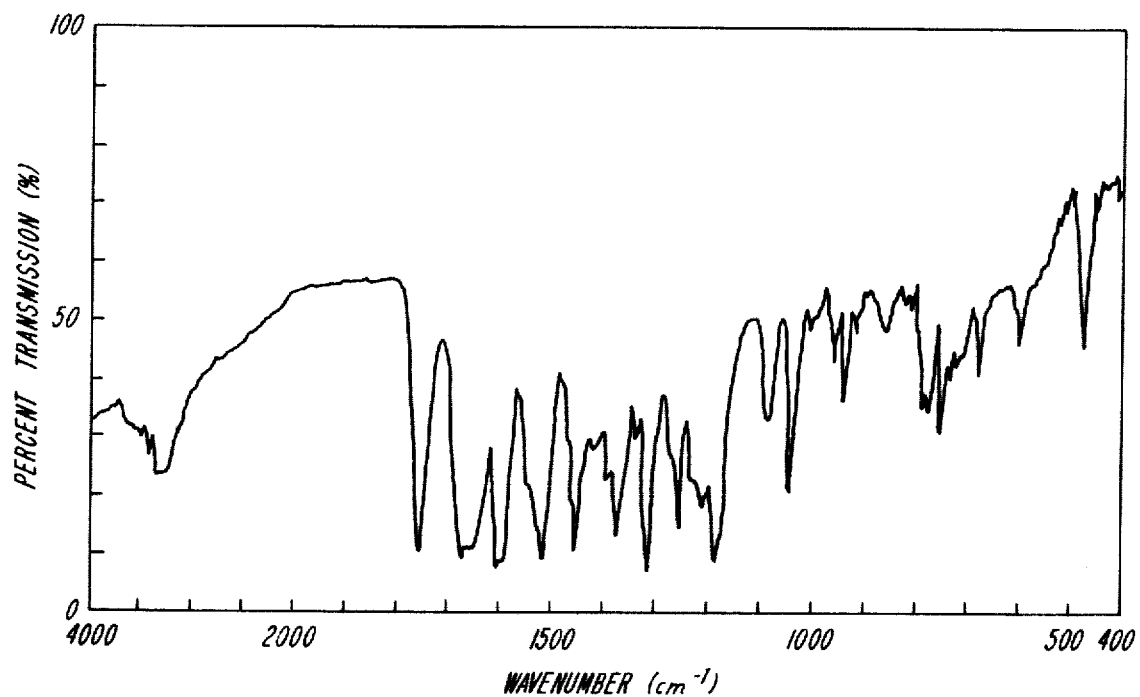
Figure 12:
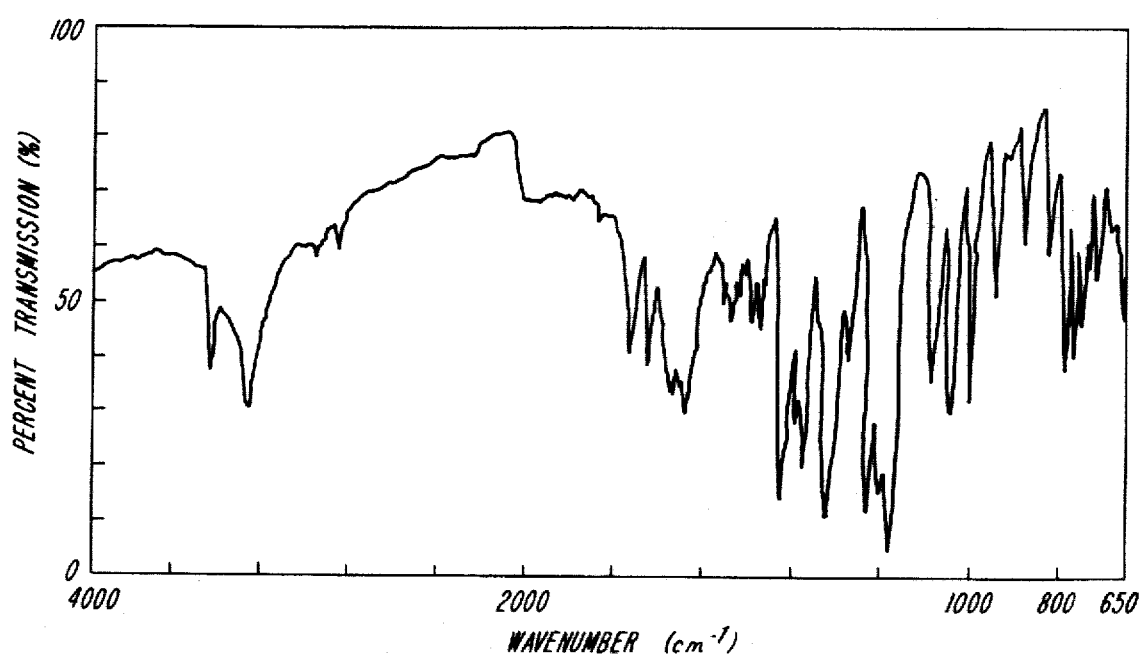
Figure 13:
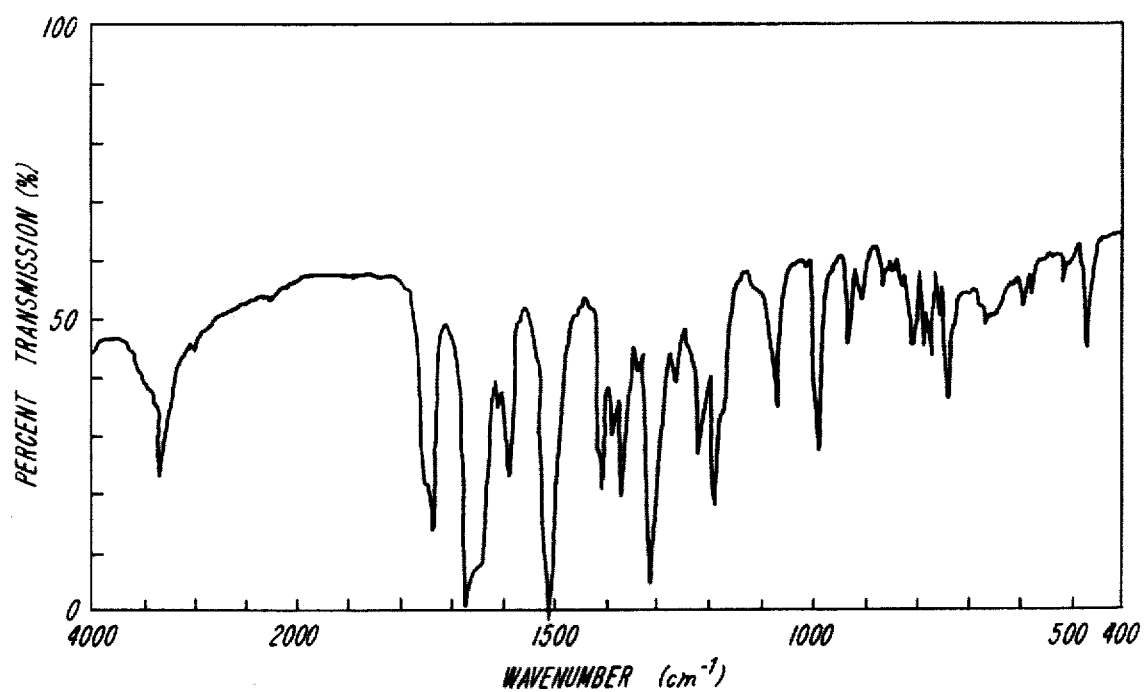
Figure 14:
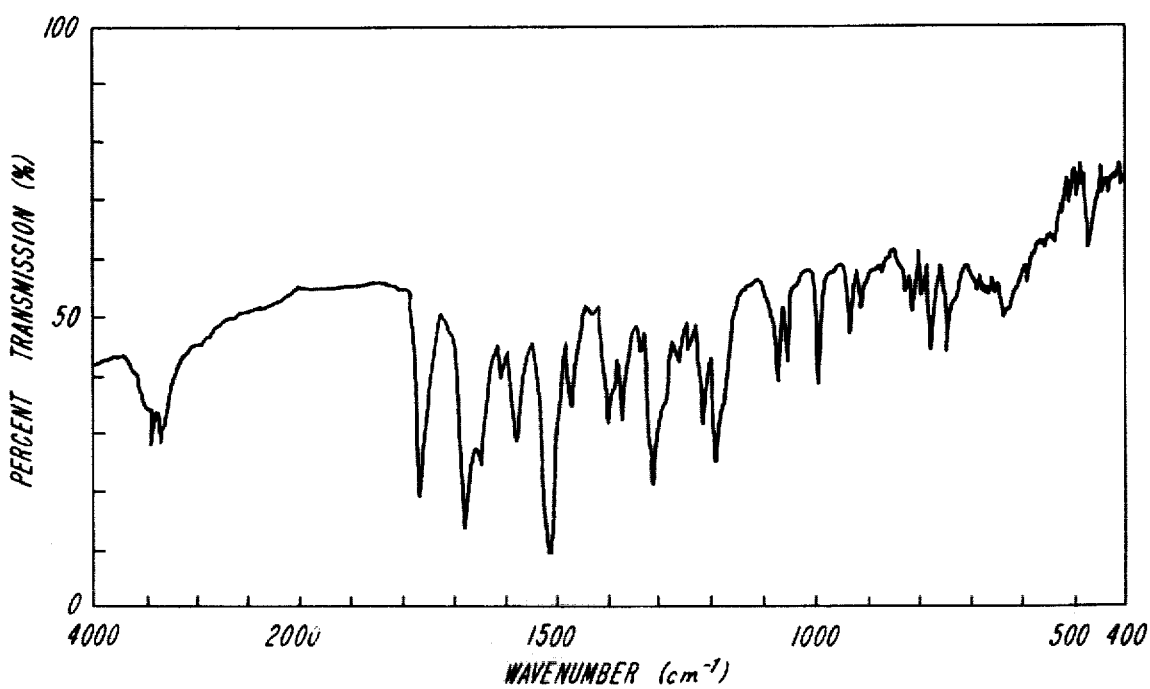
Figure 15:
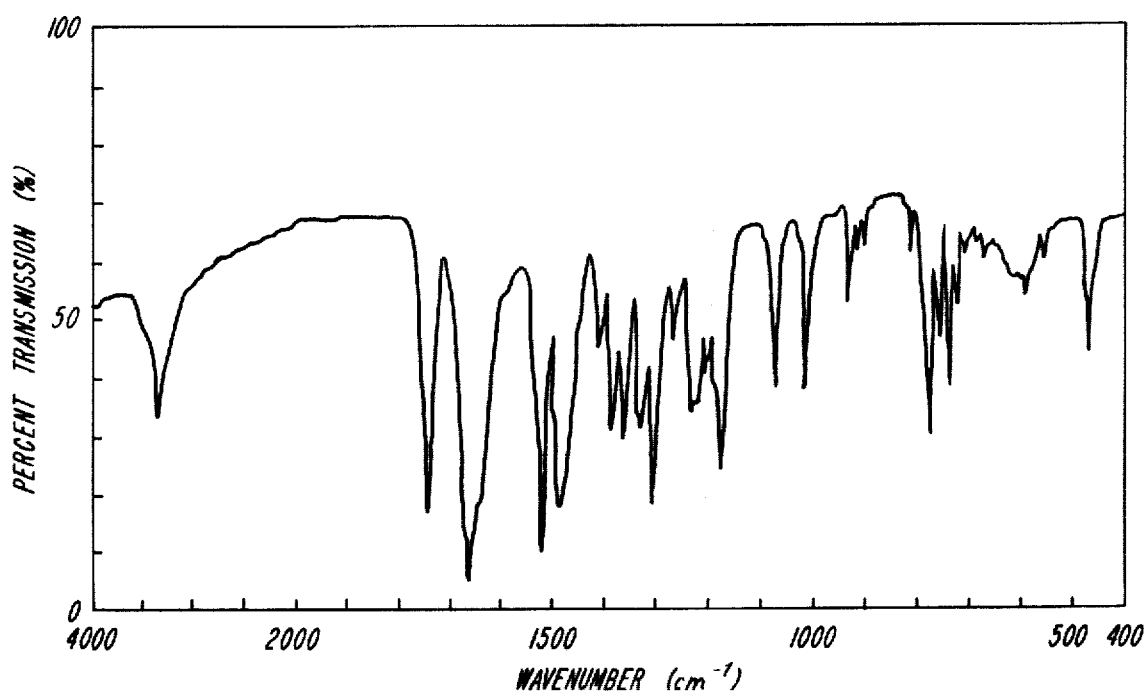
Figure 16:
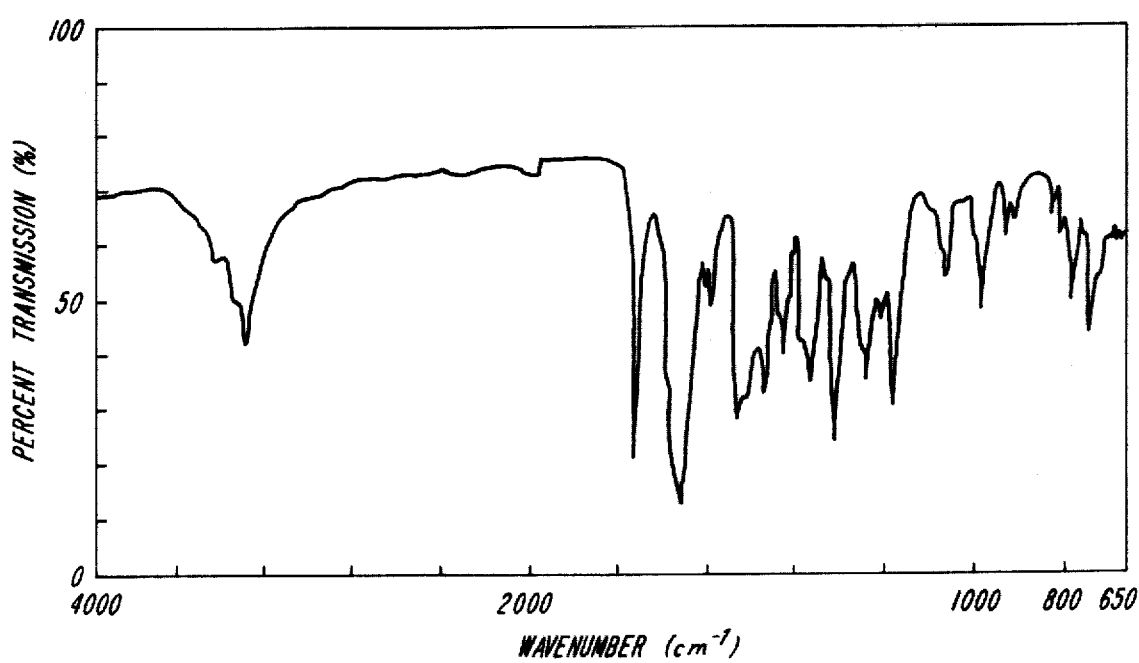
Figure 17:
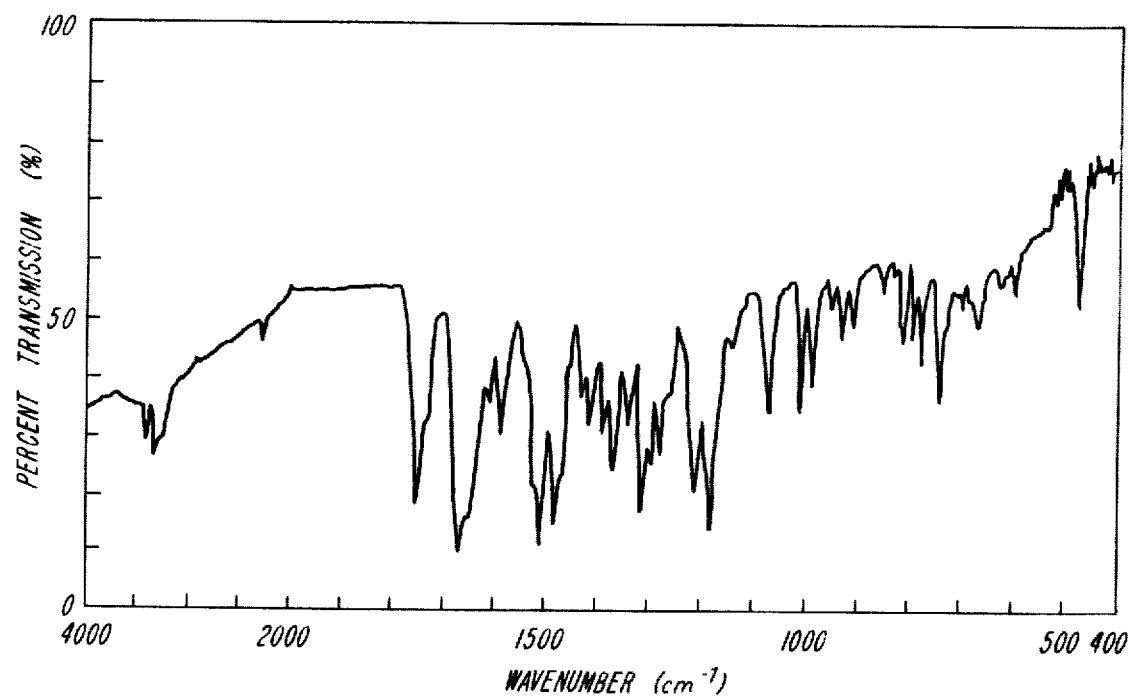
Figure 18:
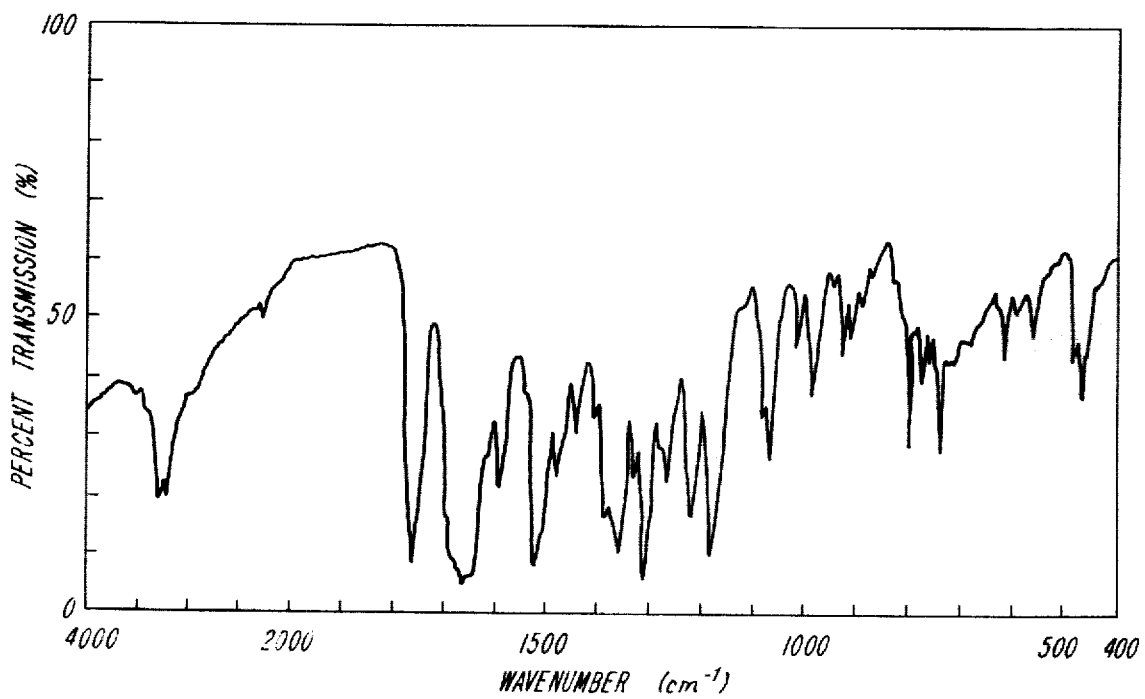
Figure 19:
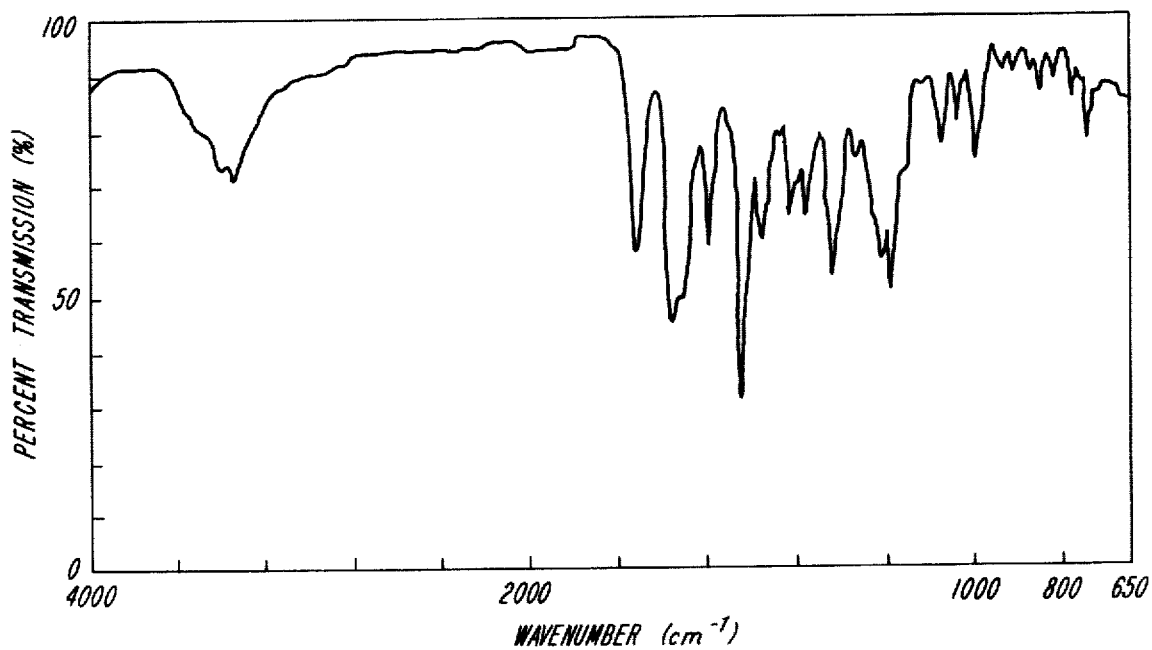
Figure 20:
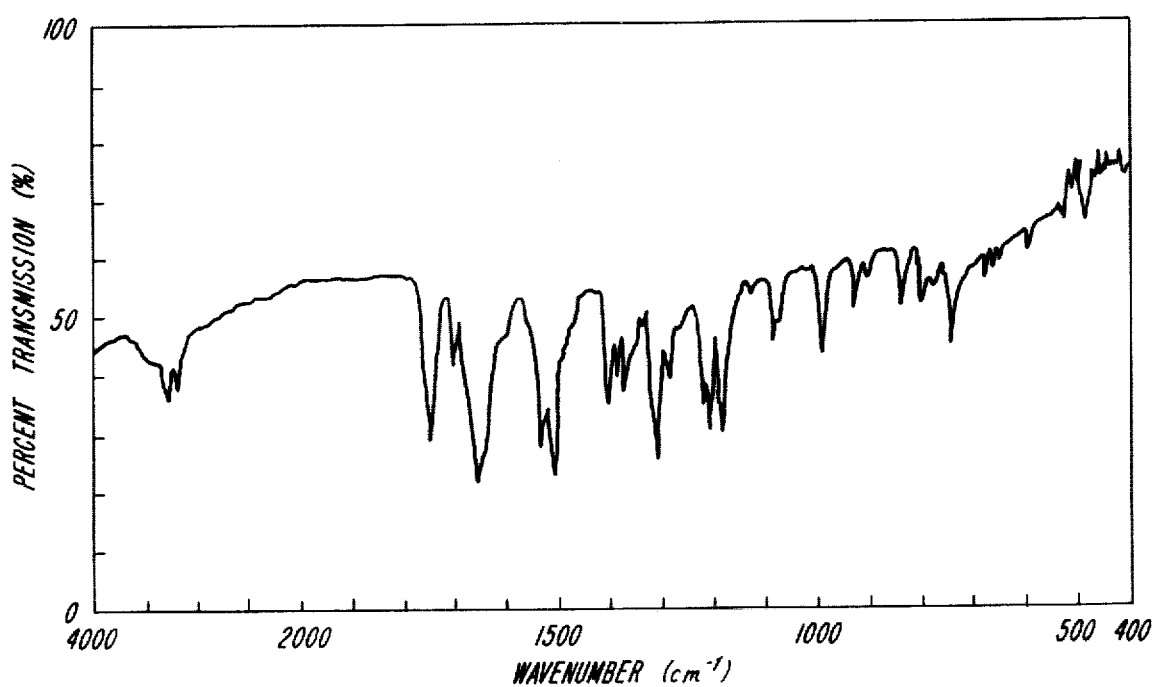

| Example No. | 3-Iminoisoindoline Compound Amount (g) | Diisocyanate Compound Amount (g) | Solvent Amount (g) | Reaction Temperature (°C.) | Condition Time (Hr) | Product Color | Yield (%) | Elementary Analysis | Calculated (%) | Found (%) | Infrared Absorption Spectrum |
|---|---|---|---|---|---|---|---|---|---|---|---|
|  | 10.0 | 3.35 |  |  |  |  |  | O:<br>Cl:<br>S: | 10.6<br>37.5<br>— | 10.5<br>37.8<br>— |  |
| 11 | 3-Imino-4,5,6,7-tetrachloro-isoindoline-1-one<br><br>10.0 | 2,5-Dichloro-p-phenylene diisocyanate<br><br>4.03 | Chlorobenzene<br><br>200 | 90 | 6 | Yellow | 96 | C:<br>H:<br>N:<br>O:<br>Cl:<br>S: | 36.1<br>0.8<br>10.5<br>8.0<br>44.5<br>— | 36.0<br>0.9<br>10.3<br>8.2<br>44.6<br>— | FIG. 9 |
| 12 | 3-Imino-4,5,6,7-tetrachloro-isoindoline-1-one<br><br>10.0 | 2,5-Dimethyl-p-phenylene diisocyanate<br><br>3.31 | Chlorobenzene<br><br>200 | 80 | 6 | Red | 82 | C:<br>H:<br>N:<br>O:<br>Cl:<br>S: | 41.3<br>1.6<br>11.1<br>8.5<br>37.6<br>— | 41.2<br>1.8<br>10.9<br>8.5<br>37.6<br>— | FIG. 10 |
| 13 | 3-Imino-4,5,6,7-tetrachloro-isoindoline-1-one<br><br>10.0 | m-Phenylene diisocyanate<br><br>3.87 | O-DCB<br>TMHD<br><br>200<br>0.3 | 120 | 6 | Yellow | 83 | C:<br>H:<br>N:<br>O:<br>Cl:<br>S: | 39.6<br>1.1<br>11.5<br>8.8<br>39.0<br>— | 39.3<br>1.1<br>11.6<br>8.9<br>39.1<br>— | — |
| 14 | 3-Imino-4,5,6,7-tetrachloro-isoindoline-1-one<br><br>10.0 | 3,5-Chlorobenzene diisocyanate<br><br>3.42 | O-DCB<br>TMHD<br><br>200<br>0.3 | 120 | 6 | Yellow | 90 | C:<br>H:<br>N:<br>O:<br>Cl:<br>S: | 37.8<br>0.9<br>11.0<br>8.4<br>41.9<br>— | 38.5<br>0.9<br>10.8<br>8.2<br>41.6<br>— | FIG. 11 |
| 15 | 3-Imino-4,5,6,7-tetrachloro-isoindoline-1-one<br><br>10.0 | 2,5-Dimethoxy-p-phenylene diisocyanate<br><br>3.87 | O-DCB<br><br>200 | 175 | 6 | Purple | 86 | C:<br>H:<br>N:<br>O:<br>Cl:<br>S: | 39.6<br>1.5<br>10.7<br>12.2<br>36.0<br>— | 39.8<br>1.5<br>10.8<br>12.3<br>35.6<br>— | FIG. 12 |
| 16 | 3-Imino-4,5,6,7-tetrachloro-isoindoline-1-one<br><br>10.0 | 4,4'-Diphenylmethane diisocyanate<br><br>6.25 | O-DCB<br><br>200 | 175 | 6 | Yellow | 90 | C:<br>H:<br>N:<br>O:<br>Cl:<br>S: | 45.5<br>1.7<br>10.3<br>7.8<br>34.7<br>— | 46.8<br>1.5<br>10.2<br>8.2<br>33.3<br>— | FIG. 13 |
| 17 | 3-Imino-4,5,6,7-tetrachloro-isoindoline-1-one<br><br>10.0 | 3,3'-Dichloro-4,4'-diphenyl-methane diisocyanate<br>5.62 | O-DCB<br><br>200 | 175 | 6 | Yellow | 88 | C:<br>H:<br>N:<br>O:<br>Cl:<br>S: | 41.9<br>1.4<br>9.5<br>7.2<br>40.0<br>— | 41.9<br>1.5<br>9.8<br>7.0<br>39.8<br>— | FIG. 14 |
| 18 | 3-Imino-4,5,6,7-tetrachloro-isoindoline-1-one<br><br>14.2 | 1,5-Naphthalene diisocyanate<br><br>5.25 | O-DCB<br>TMHD<br><br>300<br>0.3 | 130 | 6 | Red | 94 | C:<br>H:<br>N:<br>O:<br>Cl:<br>S: | 43.2<br>1.3<br>10.8<br>8.2<br>36.5<br>— | 43.3<br>1.2<br>10.3<br>9.5<br>35.7<br>— | FIG. 15 |
| 19 | 3-Imino-4,5,6,7-tetrachloro-isoindoline-1-one<br><br>15.0 | 2,6-Toluene diisocyanate<br><br>3.06 | O-DCB<br>TMHD<br><br>300<br>0.3 | 100 | 6 | Reddish Yellow | 92 | C:<br>H:<br>N:<br>O:<br>Cl:<br>S: | 40.4<br>1.3<br>11.3<br>8.6<br>38.3<br>— | 40.4<br>1.4<br>11.3<br>8.8<br>38.1<br>— | FIG. 16 |
| 20 | 3-Imino-4,5,6,7-tetrachloro-isoindoline-1-one<br><br>10.0 | 2,7-Fluorene diisocyanate<br><br>4.37 | O-DCB<br><br>200 | 150 | 6 | Red | 93 | C:<br>H:<br>N:<br>O:<br>Cl:<br>S: | 45.6<br>1.5<br>10.3<br>7.8<br>34.8<br>— | 46.4<br>1.5<br>10.2<br>7.6<br>34.3<br>— | FIG. 17 |
| 21 | 3-Imino-4,5,6,7-tetrachloro-isoindoline-1-one<br>14.2 | 2,4-Toluene diisocyanate<br><br>4.37 | Carbon tetrachloride<br>250 | 76 | 20 | Yellow | 88 | C:<br>H:<br>N:<br>O:<br>Cl:<br>S: | 40.4<br>1.3<br>11.3<br>8.6<br>38.3<br>— | 40.9<br>1.4<br>11.4<br>8.3<br>38.0<br>— | FIG. 18 |
| 22 | 3-Imino-4,5,6,7-tetrachloro-isoindoline-1-one<br><br>10.0 | 2,5-Dimethoxy-4,4'-azobenzene diisocyanate<br>5.70 | O-DCB<br><br>200 | 175 | 6 | Red | 85 | C:<br>H:<br>N:<br>O:<br>Cl:<br>S: | 43.0<br>1.8<br>12.6<br>10.8<br>31.8<br>— | 44.0<br>1.8<br>12.3<br>10.6<br>31.3<br>— | FIG. 19 |
| 23 | 3-Imino-4,5,6,7-tetrachloro-isoindoline-1-one | p-Phenylene diisocyanate | O-DCB | 120 | 6 | Orange | 93 | C:<br>H:<br>N: | 39.6<br>1.1<br>11.5 | 39.6<br>1.0<br>11.3 | FIG. 20 |

TABLE 1-continued

Figure 21:
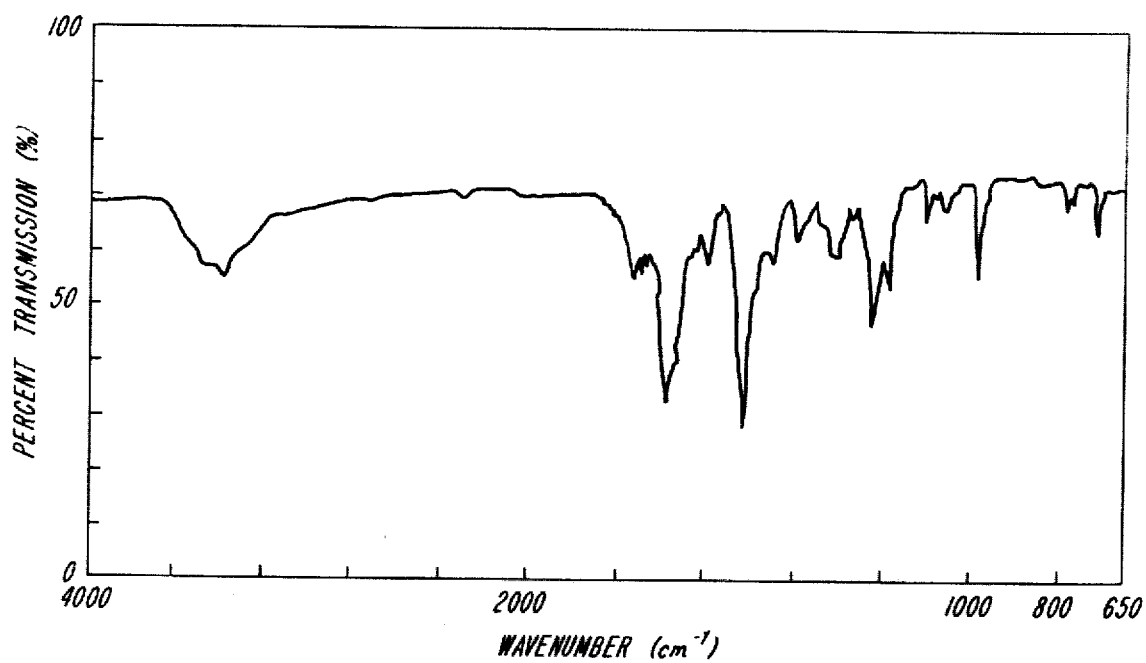
Figure 22:
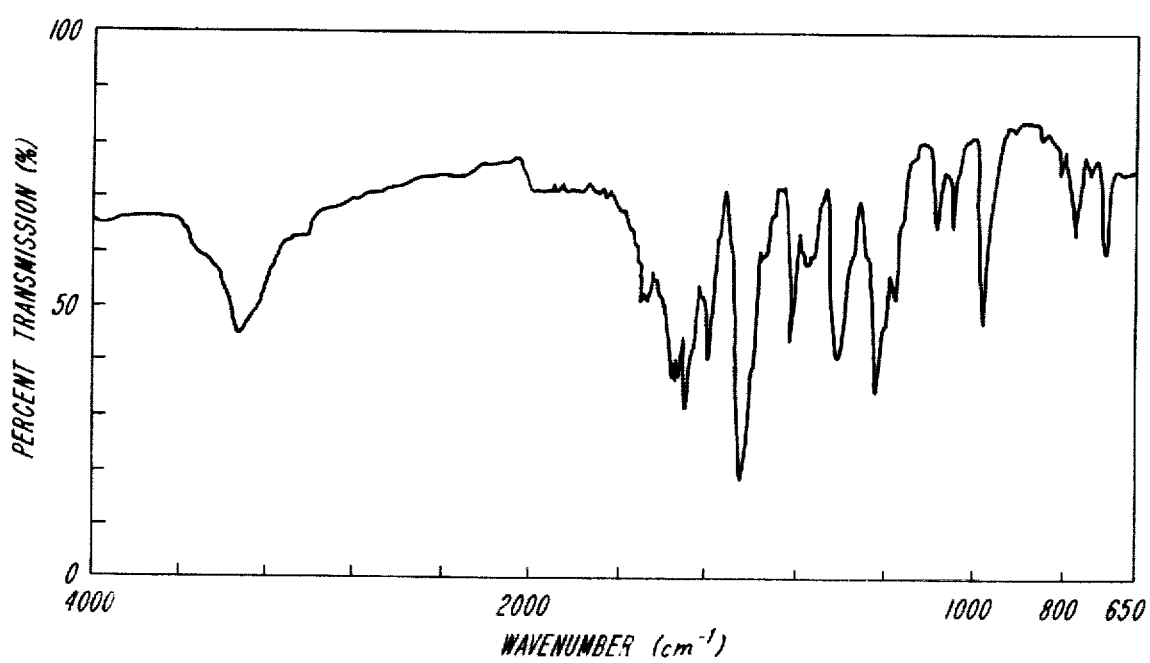

| Example No. | 3-Iminoisoindoline Compound Amount (g) | Diisocyanate Compound Amount (g) | Solvent Amount (g) | Reaction Temperature (°C.) | Condition Time (Hr) | Product Color | Yield (%) | Elementary Analysis | Calculated (%) | Found (%) | Infrared Absorption Spectrum |
|---|---|---|---|---|---|---|---|---|---|---|---|
| | 10.0 | 2.82 | 200 | | | | | O: | 8.8 | 8.9 | |
| | | | | | | | | Cl: | 39.0 | 39.2 | |
| 24 | 3-Imino-4,5,6,7-tetrachloro-isoindoline-1-one | 4,4'-Azobenzene diisocyanate | O-DCB | 175 | 6 | Orange | 87 | S: | — | — | — |
| | | | | | | | | C: | 43.3 | 43.5 | |
| | | | | | | | | H: | 1.4 | 1.1 | |
| | 10.0 | 4.65 | 200 | | | | | N: | 13.5 | 13.8 | |
| | | | | | | | | O: | 7.7 | 7.8 | |
| | | | | | | | | Cl: | 34.1 | 33.8 | |
| 25 | 3-Imino-isoindoline-1-one | 3,3'-Dimethyl-4,4'-Diphenyl diisocyanate | Dioxane 200 | 40 | 3 | Reddish Yellow | 98 | S: | — | — | FIG. 21 |
| | | | | | | | | C: | 69.1 | 69.1 | |
| | | | | | | | | H: | 4.3 | 4.3 | |
| | 10.0 | 9.04 | | | | | | N: | 15.1 | 15.0 | |
| | | | | | | | | O: | 11.5 | 11.6 | |
| | | | | | | | | Cl: | — | — | |
| 26 | 3-Imino-isoindoline-1-one | 4,4'-Diphenyl methane diisocyanate | Benzene 200 | 40 | 3 | Greenish Yellow | 73 | S: | — | — | FIG. 22 |
| | | | | | | | | C: | 68.6 | 68.8 | |
| | | | | | | | | H: | 4.1 | 3.8 | |
| | 10.0 | 8.56 | | | | | | N: | 15.5 | 15.7 | |
| | | | | | | | | O: | 11.8 | 11.7 | |
| | | | | | | | | Cl: | — | — | |
| 27 | 3-Imino-4,7-dichloro-isoindoline-1-one | 4,4'-Diphenyl methane diisocyanate | Toluene 200 | 80 | 3 | Yellow | 85 | S: | — | — | — |
| | | | | | | | | C: | 54.7 | 54.4 | |
| | | | | | | | | H: | 2.6 | 2.7 | |
| | | | | | | | | N: | 12.4 | 12.6 | |
| | 10.0 | 5.81 | | | | | | O: | 9.4 | 9.6 | |
| | | | | | | | | Cl: | 20.9 | 20.7 | |
| 28 | 3-Imino-4,5,6,7-tetrafluoro-isoindoline-1-one | 4,4'-Diphenyl methane diisocyanate | O-DCB 200 | 175 | 6 | Yellow | 93 | S: | — | — | — |
| | | | | | | | | C: | 54.2 | 54.7 | |
| | | | | | | | | H: | 2.0 | 2.1 | |
| | | | | | | | | N: | 12.2 | 12.1 | |
| | 10.0 | 5.73 | | | | | | O: | 9.3 | 9.1 | |
| | | | | | | | | F: | 22.2 | 22.0 | |
| 29 | 3-Imino-4,5,6,7-tetrabromo-isoindoline-1-one | 3,3'-Dimethyl-4,4'-diphenyl diisocyanate | O-DCB 200 | 175 | 6 | Red | 90 | S: | — | — | — |
| | | | | | | | | C: | 32.3 | 32.2 | |
| | | | | | | | | H: | 1.3 | 1.3 | |
| | | | | | | | | N: | 7.1 | 7.0 | |
| | 10.0 | 2.86 | | | | | | O: | 5.4 | 5.6 | |
| | | | | | | | | Br: | 53.9 | 53.9 | |
| | | | | | | | | S: | — | — | |

Note:
(1)O-DCB ; O-Dichlorobenzene
(2)DBTL ; Dibutyl tin dilaurate
(3)TMHD ; Tetramethyl-1,6-hexanediamine

TABLE 2

| Compound No.(1) | Solvent Resistance (2) | Chemical Resistance(3) | | Weather Proofing Color Difference ΔE (Lab)(4) |
|---|---|---|---|---|
| | | 5% HCl | 5% NaOH | |
| 1 | 5 | 5 | 5 | 2.1 |
| 2 | 5 | 5 | 5 | 1.5 |
| 3 | 5 | 5 | 5 | 1.9 |
| 4 | 5 | 5 | 5 | 2.6 |
| 5 | 5 | 5 | 5 | 0.7 |
| 6 | 5 | 5 | 5 | 2.3 |
| 7 | 5 | 5 | 5 | 2.0 |
| 8 | 5 | 5 | 5 | 1.7 |
| 9 | 5 | 5 | 5 | 1.9 |
| 10 | 5 | 5 | 5 | 2.2 |
| 11 | 5 | 5 | 5 | 1.6 |
| 12 | 5 | 5 | 5 | 2.5 |
| 13 | 5 | 5 | 5 | 2.7 |
| 14 | 5 | 5 | 5 | 1.2 |
| 15 | 5 | 5 | 5 | 2.0 |
| 16 | 5 | 5 | 5 | 1.2 |
| 17 | 5 | 5 | 5 | 1.0 |
| 18 | 5 | 5 | 5 | 2.5 |
| 19 | 5 | 5 | 5 | 1.4 |
| 20 | 5 | 5 | 5 | 2.6 |
| 21 | 5 | 5 | 5 | 2.7 |
| 22 | 5 | 5 | 5 | 2.4 |
| 23 | 5 | 5 | 5 | 2.1 |
| 24 | 5 | 5 | 5 | 2.5 |
| 25 | 4 | 4 | 4 | 1.4 |
| 26 | 4 | 4 | 4 | 1.5 |
| 27 | 4 | 5 | 5 | 1.6 |
| 28 | 5 | 5 | 5 | 2.6 |
| 29 | 5 | 5 | 5 | 2.4 |

Note:
(1)Compounds obtained by the methods of each example.
(2)A pigment was taken up in a test tube charged with xylene. After the test tube was shaked and kept stable, an appearance of migration was tested. Then, the pigment was taken up from xylene and put on the filter paper. An appearance of running on the filter paper was tested. The result was evaluated by five steps. 5 was the best.
(3)The same test as mentioned above (2) except that 5% solution of hydrochloric acid and 5% solution of sodium hydroxide were employed, respectively instead of xylene.
(4)A piece for examination was obtained by coating a paint which had been produced by dispersing 15 parts by weight of pigments with 100 parts by weight of melaminealkyd resin on the mild steel. Device was the dewcycle sunshine super long-life weather-meter, WEL-SUN-DC type, manufactured by SUGA TEST MACHINE COMPANY. An irradiation time was 500 hours.

What is claimed is:
1. A compound of the formula,

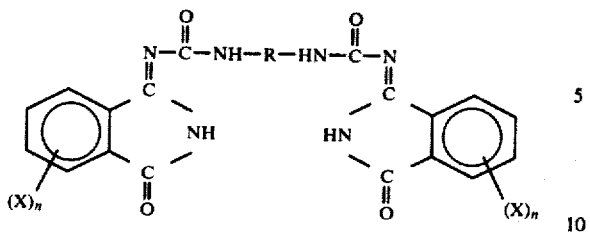

wherein R is an aromatic compound selected from the group consisting of:

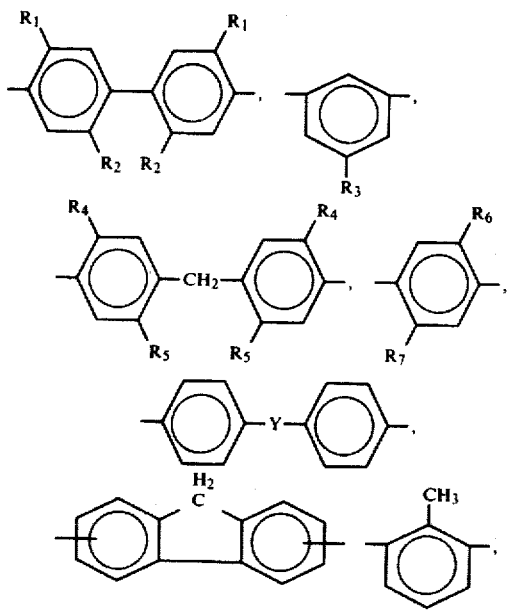

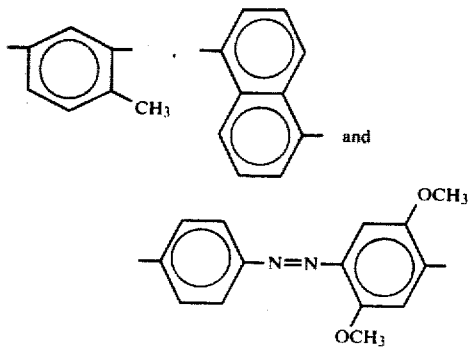

wherein $R_1$, $R_2$, $R_3$, $R_4$, $R_5 R_6$ and $R_7$, which may be the same or different, are each selected from the group consisting of hydrogen, chlorine, a $C_{1-2}$ alkyl group and a $C_{1-2}$ alkoxy group and wherein Y is $-SO_2-$, $-O-$, $-S-$, $-CO-$, $-N=N-$ or $-NHCO-$; X is a halogen atom selected from the group consisting of chlorine, bromine, and fluorine; and n is zero or an integer of from 1 to 4.

2. The compound of claim 1, wherein X is chlorine.
3. The compound of claim 2, wherein n is 4.
4. The compound of claim 3, wherein R is

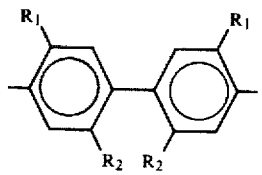

wherein $R_1$ and $R_2$ are the same as defined in claim 1; X is chlorine; and n is 4.

5. A compound in accordance with claim 4 represented by the formula,

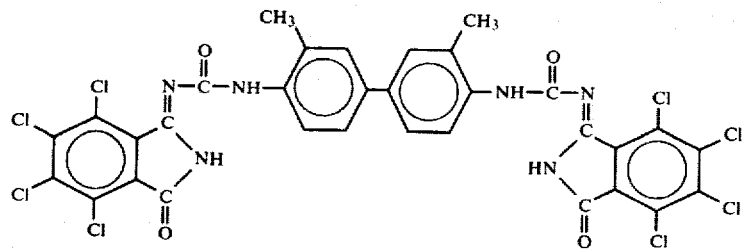

6. A compound in accordance with claim 4 represented by the formula,

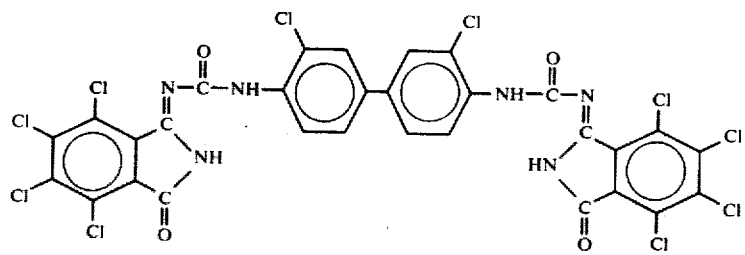

7. A compound in accordance with claim 4 represented by the formula,

8. A compound in accordance with claim 4 represented by the formula,

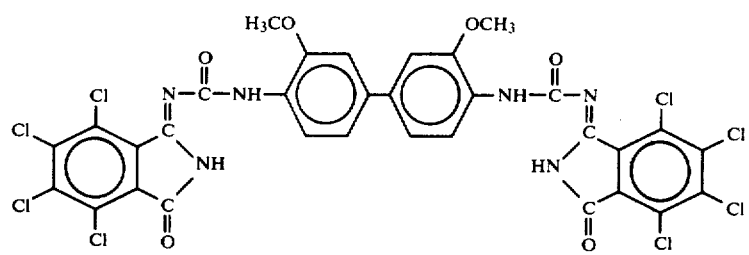

9. A compound in accordance with claim 1, wherein R is

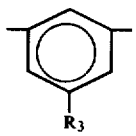

wherein $R_3$ is the same as defined in claim 1; X is chlorine; and n is 4.

10. A compound in accordance with claim 9 represented by the formula,

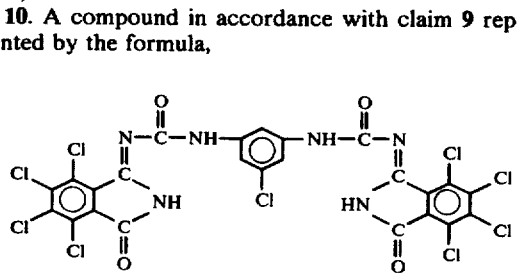

11. A compound in accordance with claim 9 represented by the formula,

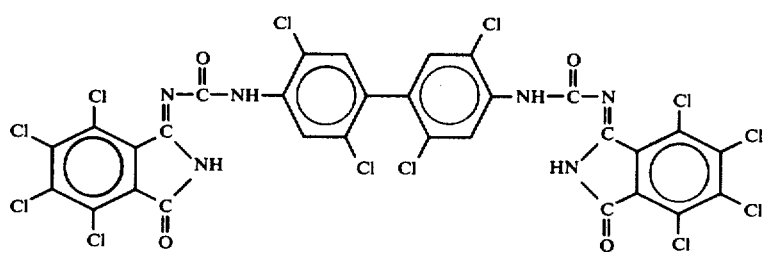

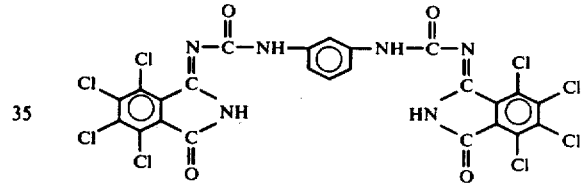

12. A compound in accordance with claim 1, wherein R is wherein $R_4$ and $R_5$ are the same as defined as in claim 1; X is chlorine and n is 4.

13. A compound in accordance with claim 12 represented by the formula,

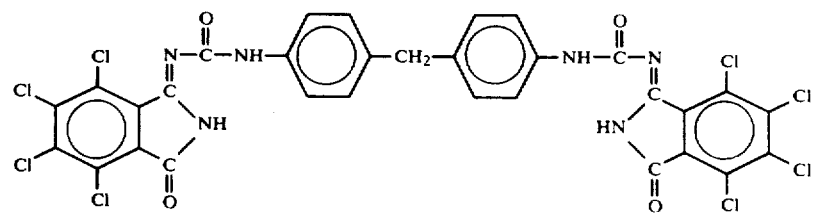

14. A compound in accordance with claim 12 represented by the formula,

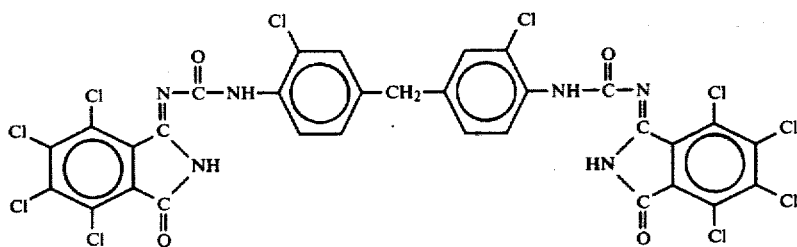

15. A compound in accordance with claim 1, wherein R is

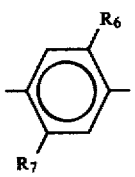

wherein $R_6$ and $R_7$ are the same as defined in claim 1; X is chlorine; and n is 4.

16. A compound in accordance with claim 15 represented by the formula,

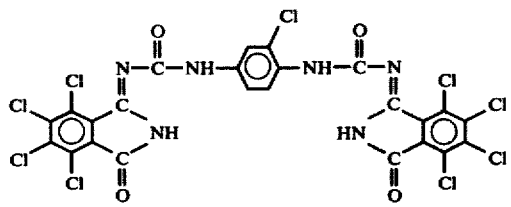

17. A compound in accordance with claim 15 represented by the formula,

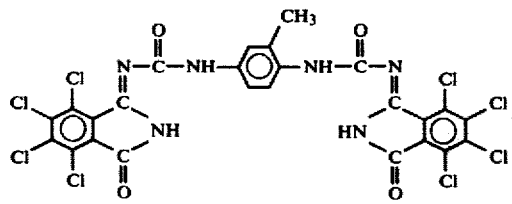

18. A compound in accordance with claim 15 represented by the formula,

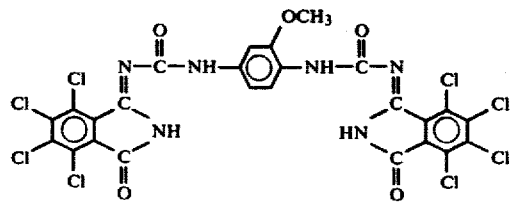

19. A compound in accordance with claim 15 represented by the formula,

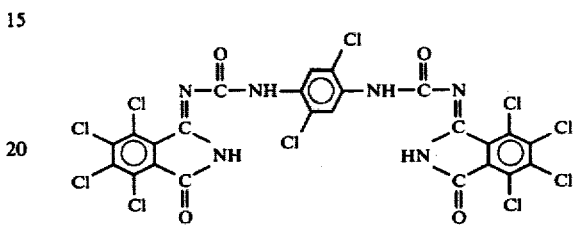

20. A compound in accordance with claim 15 represented by the formula,

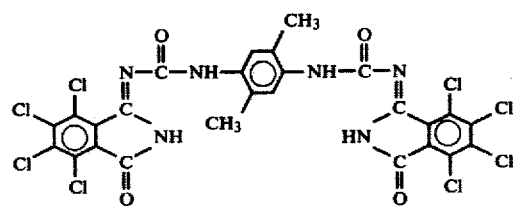

21. A compound in accordance with claim 15 represented by the formula,

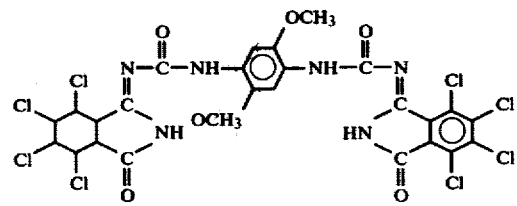

22. A compound in accordance with claim 15 represented by the formula,

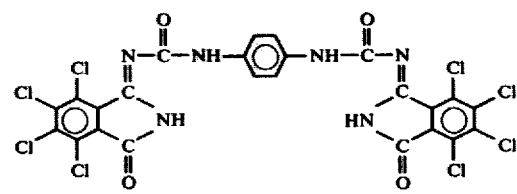

23. A compound in accordance with claim 1, wherein R is

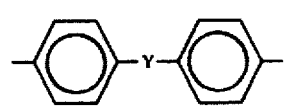

wherein Y is the same as defined in claim 1; X is chlorine; and n is 4.

24. A compound in accordance with claim 23 represented by the formula,

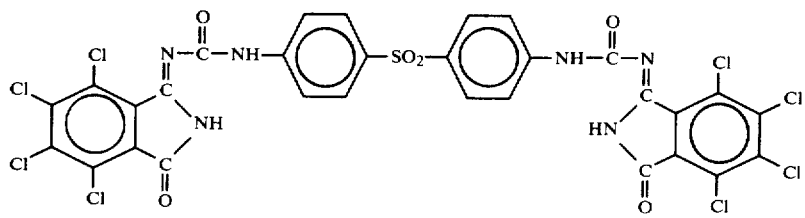

25. A compound in accordance with claim 23 represented by the formula,

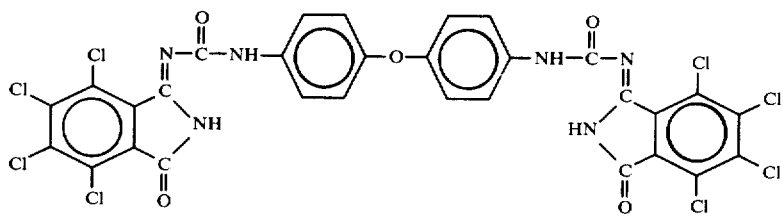

26. A compound in accordance with claim 23 represented by the formula,

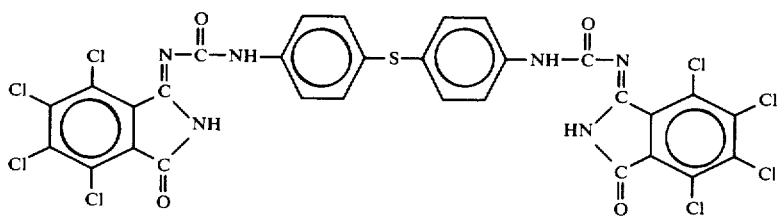

27. A compound in accordance with claim 23 represented by the formula,

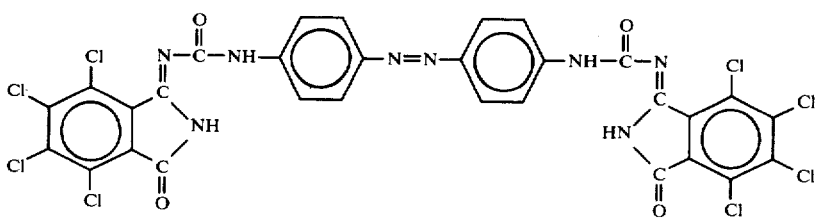

28. A compound in accordance with claim 1, wherein R is

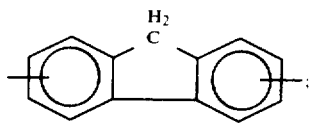

X is chlorine; and n is 4.

29. A compound in accordance with claim 28 represented by the formula,

30. A compound in accordance with claim 28 represented by the formula,

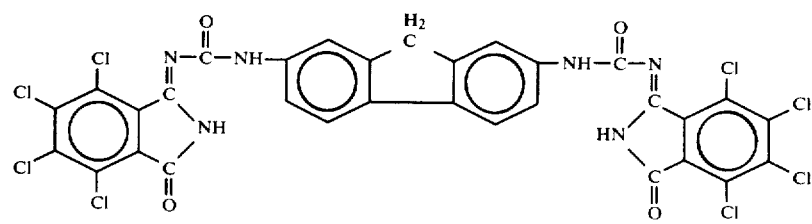

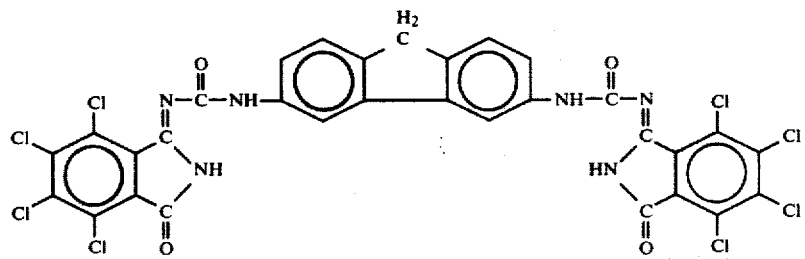

31. A compound in accordance with claim 3 represented by the formula,

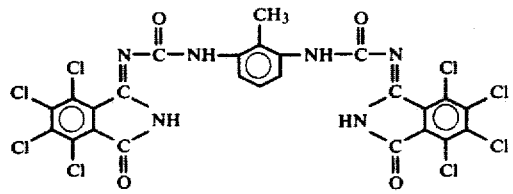

32. A compound in accordance with claim 3 represented by the formula,

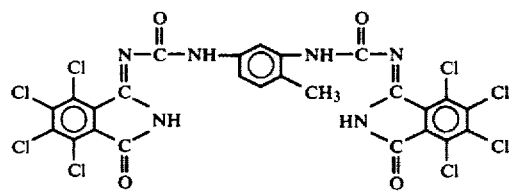

33. A compound in accordance with claim 3 represented by the formula,

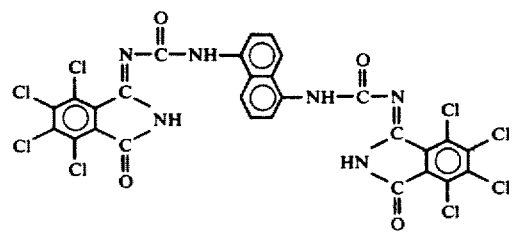

34. A compound in accordance with claim 3 represented by the formula,

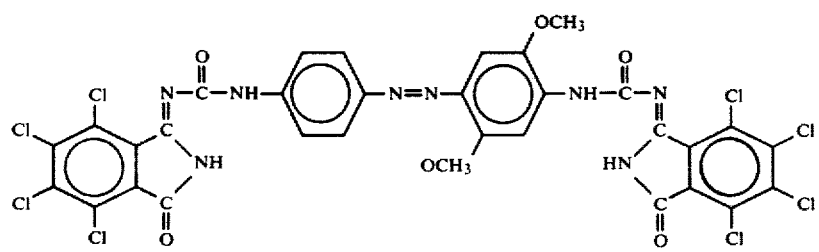

35. A compound in accordance with claim 1, wherein n is zero.

36. A compound in accordance with claim 35 represented by the formula,

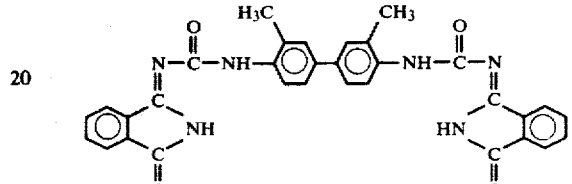

37. A compound in accordance with claim 35 represented by the formula,

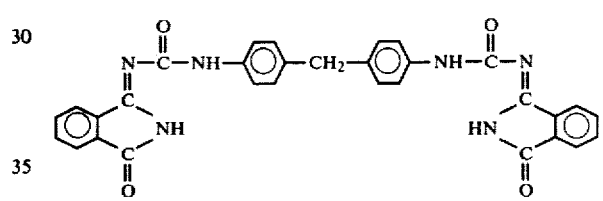

38. A compound in accordance with claim 2, wherein n is 2.

39. A compound in accordance with claim 38 represented by the formula,

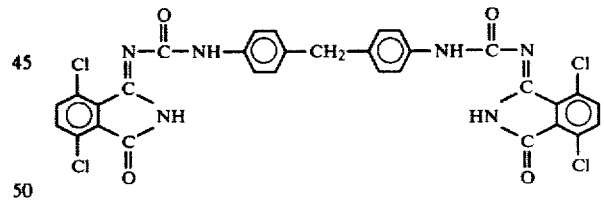

40. A compound in accordance with claim 1, wherein X is fluorine and n is 4.

41. A compound in accordance with claim 40 represented by the formula,

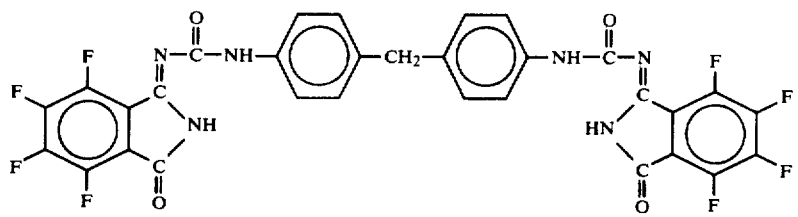
42. A compound in accordance with claim 1, wherein X is bromine and n is 4.
43. A compound in accordance with claim 42 represented by the formula,
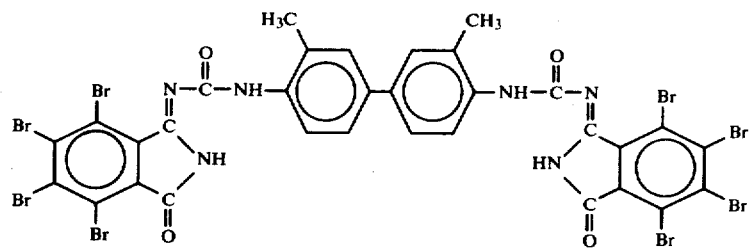
* * * * *